US011232858B2

(12) United States Patent
Gordon et al.

(10) Patent No.: US 11,232,858 B2
(45) Date of Patent: *Jan. 25, 2022

(54) COMPUTER-ASSISTED FACE-JAW-TEETH TRANSPLANTATION

(71) Applicant: THE JOHNS HOPKINS UNIVERSITY, Baltimore, MD (US)

(72) Inventors: Chad Gordon, Lutherville, MD (US); Mehran Armand, Fulton, MD (US); Ryan Murphy, Columbia, MD (US); Gerald Grant, Goshen, KY (US); Peter Liacouras, North Potomac, MD (US); Kevin Wolfe, Lutherville, MD (US)

(73) Assignees: THE JOHNS HOPKINS UNIVERSITY, Baltimore, MD (US); UNITED STATES OF AMERICA AS REPRESENTED BY THE SECRETARY OF DEFENSE, Washington, DC (US)

( * ) Notice: Subject to any disclaimer, the term of this patent is extended or adjusted under 35 U.S.C. 154(b) by 6 days.

This patent is subject to a terminal disclaimer.

(21) Appl. No.: 16/707,551

(22) Filed: Dec. 9, 2019

(65) Prior Publication Data
US 2021/0043304 A1 Feb. 11, 2021

Related U.S. Application Data

(63) Continuation of application No. 15/100,258, filed as application No. PCT/US2014/067504 on Nov. 25, 2014, now Pat. No. 10,537,337.
(Continued)

(51) Int. Cl.
*G16H 30/40* (2018.01)
*G16H 50/50* (2018.01)
(Continued)

(52) U.S. Cl.
CPC ............ *G16H 30/40* (2018.01); *A61B 17/15* (2013.01); *A61B 17/1695* (2013.01);
(Continued)

(58) Field of Classification Search
CPC ......... A61B 34/10; A61B 34/20; A61B 17/17; A61B 17/1739; A61B 17/15; G06F 19/00; G06F 19/3437
See application file for complete search history.

(56) References Cited

U.S. PATENT DOCUMENTS 3,457,922 A 7/1969 Ray et al.
4,436,684 A 3/1984 White
(Continued)

FOREIGN PATENT DOCUMENTS

WO 2012147114 A1 11/2012
WO 2013101753 A1 7/2013
WO 2014043452 3/2014

OTHER PUBLICATIONS

Bell, R. B., "Computer Planning and Intraoperative Navigation in Orthognathic Surgery"; Journal of Oral and Maxillofacial Surgery; 2011, vol. 69, No. 3, pp. 592-605.
(Continued)

*Primary Examiner* — Christopher J Beccia
(74) *Attorney, Agent, or Firm* — MH2 Technology Law Group, LLP

(57) ABSTRACT

A computer-assisted surgical system can include a donor sub-system and a recipient sub-system. The donor sub-system includes a first reference unit having a first trackable element, a fragment reference unit having a second trackable element, and a first detector configured to provide at least one of a first signal corresponding to a detected location of one or more of the first trackable element and the second trackable element. The recipient sub-system includes a sec-
(Continued)

ond reference unit having a third trackable element, and a second detector configured to provide at least one of a second signal corresponding to a detected location of at least the third trackable element.

11 Claims, 25 Drawing Sheets

Related U.S. Application Data

(60) Provisional application No. 61/910,204, filed on Nov. 29, 2013, provisional application No. 61/940,196, filed on Feb. 14, 2014, provisional application No. 62/049,866, filed on Sep. 12, 2014.

(51) Int. Cl.
| | |
|---|---|
| *A61B 17/17* | (2006.01) |
| *G16H 20/40* | (2018.01) |
| *A61B 34/10* | (2016.01) |
| *A61B 34/20* | (2016.01) |
| *A61B 17/15* | (2006.01) |
| *A61B 17/16* | (2006.01) |
| *A61B 17/80* | (2006.01) |
| *A61F 2/28* | (2006.01) |

(52) U.S. Cl.
CPC ........ *A61B 17/176* (2013.01); *A61B 17/1739* (2013.01); *A61B 17/8085* (2013.01); *A61B 34/10* (2016.02); *A61B 34/20* (2016.02); *A61F 2/2803* (2013.01); *G16H 20/40* (2018.01); *G16H 50/50* (2018.01); *A61B 2034/105* (2016.02); *A61B 2034/108* (2016.02); *A61B 2034/2051* (2016.02); *A61B 2034/2055* (2016.02); *A61B 2034/2065* (2016.02); *Y02A 90/10* (2018.01)

(56) References Cited

U.S. PATENT DOCUMENTS

| | | | |
|---|---|---|---|
| 5,279,575 | A | 1/1994 | Sugarbaker |
| 5,741,215 | A | 4/1998 | DUrso |
| 5,752,962 | A | 5/1998 | D'Urso |
| 5,810,712 | A | 9/1998 | Dunn |
| 5,951,498 | A | 9/1999 | Arnett |
| 6,079,681 | A | 6/2000 | Stern et al. |
| 6,112,109 | A | 8/2000 | DUrso |
| 6,120,290 | A | 9/2000 | Fukushima et al. |
| 6,226,548 | B1 | 5/2001 | Foley et al. |
| 6,254,639 | B1 | 7/2001 | Peckitt |
| 6,285,902 | B1 | 9/2001 | Kienzle, III et al. |
| 6,491,699 | B1 | 12/2002 | Henderson et al. |
| 6,500,179 | B1 | 12/2002 | Masini |
| 6,608,628 | B1 | 8/2003 | Ross et al. |
| 6,726,678 | B1 | 4/2004 | Nelson et al. |
| 6,796,986 | B2 | 9/2004 | Duffner |
| 6,845,175 | B2 | 1/2005 | Kopelman et al. |
| 6,932,842 | B1 | 8/2005 | Litschko et al. |
| 7,050,877 | B2 | 5/2006 | Iseki et al. |
| 7,113,841 | B2 | 9/2006 | Abe et al. |
| 7,510,557 | B1 | 3/2009 | Bonutti |
| 7,596,399 | B2 | 9/2009 | Singhal et al. |
| 7,747,305 | B2 | 6/2010 | Dean et al. |
| 7,747,318 | B2 | 6/2010 | John et al. |
| 7,792,341 | B2 | 9/2010 | Schutyser |
| 7,857,821 | B2 | 12/2010 | Couture et al. |
| 7,953,260 | B2 | 5/2011 | Weinzweig et al. |
| 8,086,336 | B2 | 12/2011 | Christensen |
| 8,096,997 | B2 | 1/2012 | Plaskos et al. |
| 8,221,430 | B2 | 7/2012 | Park et al. |
| 8,221,461 | B2 | 7/2012 | Kuiper et al. |
| 8,357,165 | B2 | 1/2013 | Grant et al. |
| 8,397,732 | B2 | 3/2013 | Singhal et al. |
| 8,403,934 | B2 | 3/2013 | Angibaud et al. |
| 8,428,315 | B2 | 4/2013 | Suetens et al. |
| 8,518,085 | B2 | 8/2013 | Winslow et al. |
| 8,535,063 | B1 | 9/2013 | Amato |
| 8,650,005 | B2 | 2/2014 | Liao |
| 8,706,285 | B2 | 4/2014 | Narainasamy et al. |
| 8,781,557 | B2 | 7/2014 | Dean et al. |
| 8,827,932 | B2 | 9/2014 | Hirabayashi |
| 9,208,558 | B2 | 12/2015 | Dean et al. |
| 9,216,084 | B2 | 12/2015 | Gordon et al. |
| 9,330,206 | B2 | 5/2016 | Dean et al. |
| 9,659,152 | B2 | 5/2017 | Mueller |
| 10,537,337 | B2 * | 1/2020 | Gordon ................ A61B 17/176 |
| 2001/0021851 | A1 | 9/2001 | Eberlein et al. |
| 2002/0035458 | A1 | 3/2002 | Kim et al. |
| 2002/0165552 | A1 | 11/2002 | Duffner |
| 2002/0169485 | A1 | 11/2002 | Pless et al. |
| 2004/0091845 | A1 | 5/2004 | Azerad et al. |
| 2004/0172044 | A1 | 9/2004 | Grimm et al. |
| 2004/0204760 | A1 | 10/2004 | Fitz et al. |
| 2005/0043835 | A1 | 2/2005 | Christensen |
| 2005/0113846 | A1 | 5/2005 | Carson |
| 2005/0117696 | A1 | 6/2005 | Suzuki et al. |
| 2006/0142657 | A1 | 6/2006 | Quaid et al. |
| 2006/0195111 | A1 | 8/2006 | Couture |
| 2007/0167701 | A1 | 7/2007 | Sherman |
| 2007/0207441 | A1 | 9/2007 | Lauren |
| 2007/0225773 | A1 | 9/2007 | Shen et al. |
| 2008/0140149 | A1 | 6/2008 | John et al. |
| 2008/0304725 | A1 | 12/2008 | Leitner |
| 2008/0306490 | A1 | 12/2008 | Lakin et al. |
| 2008/0319448 | A1 | 12/2008 | Lavallee et al. |
| 2009/0088674 | A1 * | 4/2009 | Caillouette ............ A61B 6/56 602/26 |
| 2009/0092948 | A1 | 4/2009 | Gantes |
| 2009/0099570 | A1 | 4/2009 | Paradis et al. |
| 2009/0112273 | A1 | 4/2009 | Wingeier et al. |
| 2009/0220122 | A1 | 9/2009 | Richards et al. |
| 2009/0240141 | A1 * | 9/2009 | Neubauer .......... A61B 17/1684 600/426 |
| 2009/0281623 | A1 | 11/2009 | Kast et al. |
| 2009/0311647 | A1 | 12/2009 | Fang et al. |
| 2010/0145425 | A1 | 6/2010 | Jung et al. |
| 2010/0145898 | A1 | 6/2010 | Malfliet et al. |
| 2010/0261998 | A1 | 10/2010 | Stiehl |
| 2010/0311028 | A1 | 12/2010 | Bell et al. |
| 2011/0029093 | A1 | 2/2011 | Bojarski et al. |
| 2011/0066072 | A1 | 3/2011 | Kawoos et al. |
| 2011/0087465 | A1 | 4/2011 | Mahfouz |
| 2011/0102549 | A1 | 5/2011 | Takahashi |
| 2011/0117530 | A1 | 5/2011 | Albocher et al. |
| 2011/0196377 | A1 | 8/2011 | Hodorek et al. |
| 2011/0208256 | A1 | 8/2011 | Zuhars |
| 2011/0244415 | A1 | 10/2011 | Batesole |
| 2012/0041318 | A1 | 2/2012 | Taylor |
| 2012/0041446 | A1 | 2/2012 | Wong et al. |
| 2012/0063655 | A1 | 3/2012 | Dean et al. |
| 2012/0109228 | A1 | 5/2012 | Boyer et al. |
| 2012/0230568 | A1 | 9/2012 | Grbic et al. |
| 2012/0259592 | A1 | 10/2012 | Liao |
| 2013/0035690 | A1 | 2/2013 | Mittelstadt et al. |
| 2013/0122463 | A1 | 5/2013 | Csillag |
| 2013/0204600 | A1 | 8/2013 | Mehra |
| 2013/0211424 | A1 | 8/2013 | Thiran et al. |
| 2013/0211792 | A1 | 8/2013 | Kang et al. |
| 2013/0217996 | A1 | 8/2013 | Finkelstein et al. |
| 2013/0296872 | A1 | 11/2013 | Davison et al. |
| 2013/0297265 | A1 | 11/2013 | Baloch et al. |
| 2013/0310963 | A1 | 11/2013 | Davison |
| 2014/0045167 | A1 | 2/2014 | Anderson et al. |
| 2014/0122382 | A1 | 5/2014 | Elster et al. |
| 2014/0127639 | A1 | 5/2014 | Hirabayashi |
| 2014/0329194 | A1 | 11/2014 | Sachdeva et al. |
| 2014/0343557 | A1 | 11/2014 | Mueller |
| 2015/0272691 | A1 | 10/2015 | Kim et al. |
| 2015/0297309 | A1 | 10/2015 | Bly et al. |
| 2015/0328004 | A1 | 11/2015 | Mafhouz |
| 2016/0038243 | A1 | 2/2016 | Miller et al. |

(56) References Cited

U.S. PATENT DOCUMENTS

| | | |
|---|---|---|
| 2016/0045317 A1 | 2/2016 | Lang et al. |
| 2016/0324664 A1 | 11/2016 | Piron et al. |
| 2016/0346091 A1 | 12/2016 | Bin Abdul Rahman et al. |
| 2017/0014169 A1 | 1/2017 | Dean et al. |
| 2017/0108930 A1 | 4/2017 | Banerjee et al. |
| 2017/0273797 A1 | 9/2017 | Gordon et al. |

OTHER PUBLICATIONS

Cevidances, L. et al. Three-dimensional surgical simulation:, American Journal of Orhodontics and Dentofacial Orhopedics, vol. 138, Issue 3, Sep. 2010, pp. 361-371 (Year:2010).
Chapuis et al., "A new approach for 3D computer-assisted orthognathic surgery-first clinical case", Elsevier, International Congress Serier, vol. 1281, May 2005, pp. 1217-1222 (Year: 2005).
Chapuis, J. et al., "A New System for Computer-Aided Preoperative Planning and Intraoperative Navigation During Corrective Jaw Surgery", IEEE, Transactions on Information Technology in Biomedicine, vol. 11, No. 3, May 2007, pp. 274-287 (Year: 2007).
Extended European Search Report dated Jul. 27, 2018 in corresponding EP Application No. 15862375, 8 pages.
Extended European Search Report dated May 24, 2018 in corresponding EP Application No. 15862868, 8 pages.
Goh, R. et al., "Customized fabricated implats after previous failed cranioplasty", Journal of Plastic, Reconstructive and Aesthetic Surgery, vol. 63, 2010, pp. 1479-1484.
International Search Report and Written Opinion in International Application No. PCT/US2015/062521, 12 pages.
International Search Report and Written Opinion dated Mar. 9, 2015 from corresponding International Application No. PCT/US2014/067671; 13 pages.
International Search Report and Written Opinion in International Application No. PCT/US2015/062516, 10 pages.
International Search Report and Written Opinion dated Sep. 12, 2016 for PCT/US2016/030447.
International Search Report dated Mar. 13, 2015 from corresponding International Application No. PCT/US2014/067167; 5 pgs.
International Search Report dated Mar. 20, 2015 from corresponding International Application No. PCT/US2014/067692; 4 pgs.
International Search Report dated Mar. 5, 2015 from corresponding International Application No. PCT/US2014/067174; 4 pgs.
International Search Report dated Mar. 5, 2015 from corresponding International Application No. PCT/US2014/067656; 5 pgs.
International Search Reported dated Feb. 27, 2015 from corresponding International Application No. PCT/US2014/067581; 4 pgs.
Jalbert et al., "One-step primary reconstruction for complex craniofacial re section with PEEK custom-made implants", Jounal of Cranio-Maxillo-Facial Surgery, Mar. 2014, vol. 42, No. 2, pp. 141-148.
Lee, M. et al., "Custom implant design for patients with craniel defects", Engineering in Medicine and Biology Magazine, IEEE, 2002, vol. 21, pp. 38-44.
Molla: "General Principles of Bone Grafting in Maxillofacial Surgery"; Jan. 2001; The ORION vol. 8; https://pdfs.semanticsholar.org/ec2e/7ba90a835e873687d9454a848842f26c4.pdf.
Murphy et al., "Computer-assisted single-stage cranioplasty", IN: Engineering in Medicine and Biology Sociaty (EMBC), Aug. 25-29, 2015, pp. 4910-4912.
Schramm et al.; "Non-invasive Registration in Computer Assisted Craniomaxillofacial Surgery"; Rechner-und Sensorgestutzte Chirurgie, 2001, pp. 258-268.
Examination Report in Australian Corresponding Application No. 2015353601 dated Jul. 29, 2019, 4 pages.
International Search Report dated Feb. 24, 2015 from corresponding International Application No. PCT/US2014/067504; 5 pgs.
Gordon et al.; "Overcoming Cross-Gender Differences and Challenges in Le Fort-Based, Craniomaxillofacial Transplantation With Ehanced Computer-Assisted Technology"; Annals of Plastic Surgery; Oct. 2013, vol. 71, No. 4; pp. 421-428.
Murphy et al. "Computer-Assisted, Le Fort-Based, Face-Jaw-Teeth Transplantation: A Pilot Study on System Feasiblity and Translational Assessment." International journal of computer assisted radiology and surgery, 2014.
Australian Examination Report in AU Application No. 2015353523 dated Jun. 28, 2019, 3 pages.
Chinese Office Action in CN Application No. 2016800512990 dated Jun. 18, 2019, 6 pages.
European Search Report in EP Application No. 16842453.9 dated Apr. 16, 2019, 8 pages.
Non-Final Office Action in corresponding U.S. Appl. No. 15/529,036 dated Apr. 27, 2021, 24 pages.

* cited by examiner

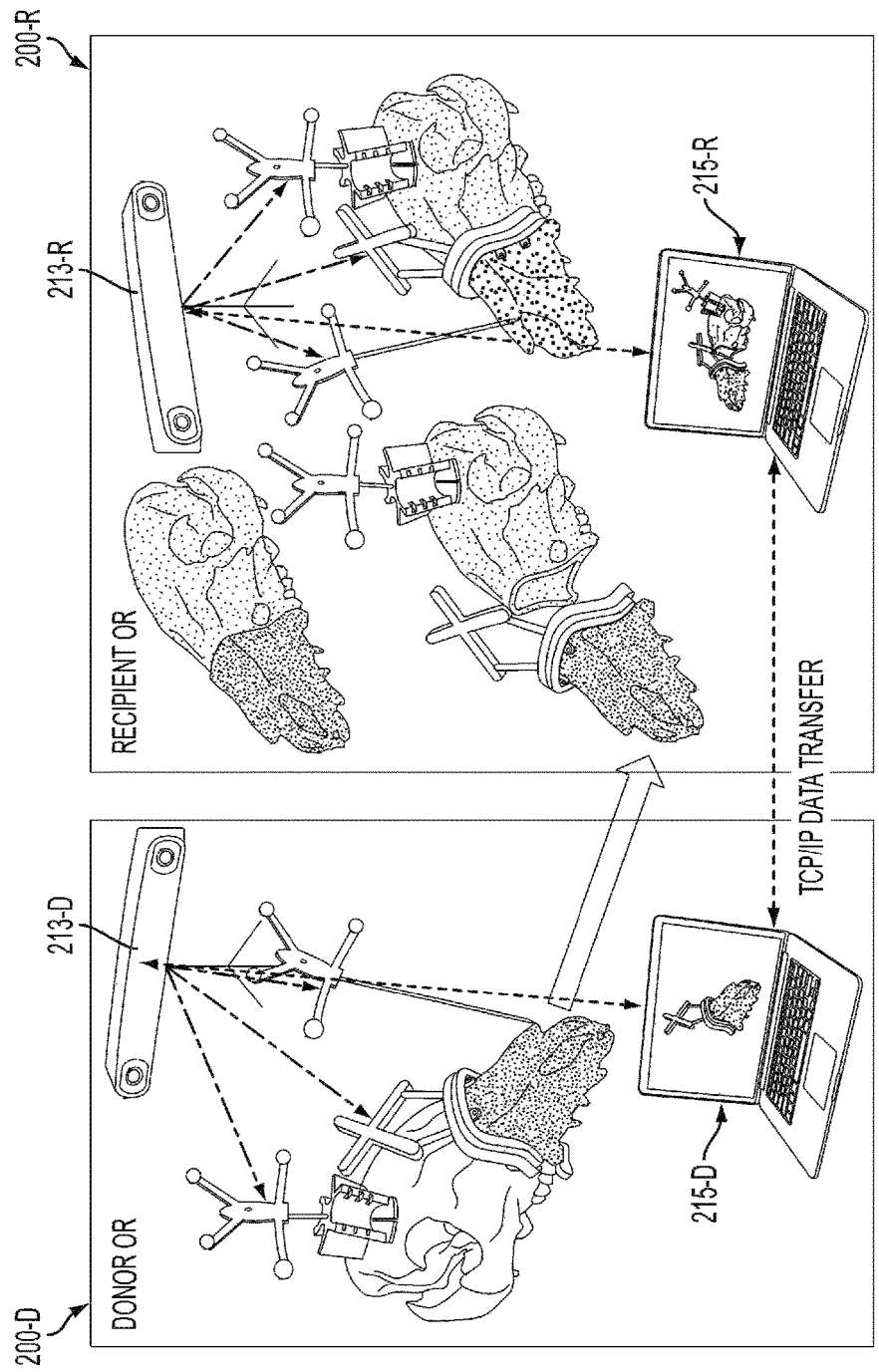
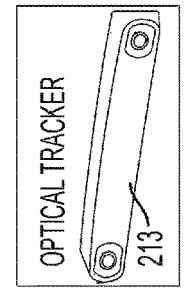
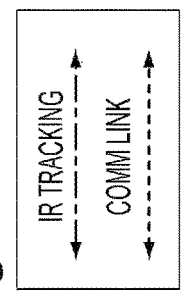
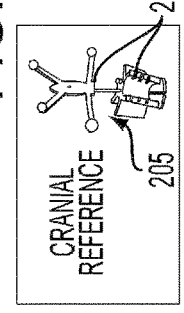
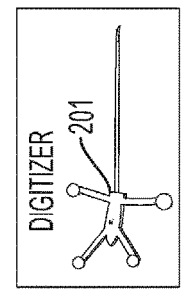

| | |
|---|---|
| LIB-PA-ALV | 8° |
| PA-PRN-ALV | 105° |
| PA-PRN-LIB | 89° |
| ALV-PRN-LIB | 16° |
| OCC-PRN | 184 |
| ZY-ZY | 84 |
| PA-PRN | 191 |
| Go-Gn | 62 |
| Go-LIB | 90 |
| PA-ALV | 197 |
| LIB-ALV | 35 |
| Overbite | -10 |
| Overjet | -7 |

| | |
|---|---|
| LIB-PA-ALV | 7° |
| PA-PRN-ALV | 112° |
| PA-PRN-LIB | 84° |
| ALV-PRN-LIB | 28° |
| OCC-PRN | 186 |
| ZY-ZY | 84 |
| PA-PRN | 191 |
| Go-Gn | 62 |
| Go-LIB | 90 |
| PA-ALV | 200 |
| LIB-ALV | 27 |
| Overbite | -2 |
| Overjet | -3 |

COMPUTER-ASSISTED FACE-JAW-TEETH TRANSPLANTATION

CROSS-REFERENCE TO RELATED APPLICATIONS

This application is a Continuation of application Ser. No. 15/100,258, filed May 27, 2016, now U.S. Pat. No. 10,537,337 which is a U.S. National Stage application of PCT/US2014/067504 filed 25 Nov. 2014, which claims priority to U.S. Provisional patent application 61/910,204 filed 29 Nov. 2013, U.S. provisional application 61/940,196 filed 14 Feb. 2014, and U.S. provisional application 62/049,866 filed 12 Sep. 2014, the entire disclosures of which are hereby incorporated by reference in their entireties.

GOVERNMENT SUPPORT STATEMENT

This invention was made with government support under Grant Nos. TR000424 and TR001079 awarded by the National Institutes of Health (NIH). The government has certain rights in the invention.

FIELD OF THE INVENTION

This invention relates generally to the field of surgery, particularly craniomaxillofacial surgery, and specifically to the field of computer-assisted craniomaxillofacial surgery and all related orthognathic, neurosurgical and head/face/neck surgical procedures and associated methods, tools, and systems.

BACKGROUND OF THE INVENTION

Facial transplantation represents one of the most complicated scenarios in craniomaxillofacial surgery due to skeletal, aesthetic, and dental discrepancies between donor and recipient. Use of computer technology to improve accuracy and precision of craniomaxillofacial surgical procedures has been described for nearly 30 years, since the increasing availability of computed topography (CT) prompted the development of a CT-based surgical simulation plan for osteotomies.

Two broad approaches to computer-assisted surgery (CAS) have gained popularity: 1) pre-operative computer surgical planning and the use of three-dimensional computer manufactured surgical guides (3D CAD/CAM) to cut and reposition bone and soft tissue, and 2) utilizing intraoperative feedback relative to preoperative imaging for the surgeon to provide more objective data on what is happening beyond the "eyeball test." However, none are meant for real-time placement feedback in areas where guide placement is more challenging, such as the three-dimensional facial skeleton. Also, there are no single platforms built to provide BOTH planning AND navigation—with seamless integration. Additionally, standard off-the-shelf vendor computer-assisted surgery systems may not provide custom features to mitigate problems associated with the increased complexity of this particular procedure. Furthermore, there are currently no validated methods for optimizing outcomes related to facial (e.g., soft tissue), skeletal (e.g., hard tissue), and occlusal (e.g., dental) inconsistencies in the setting of donor-to-recipient anthropometric mismatch—a major hurdle to achieving this specialty's full potential.

One known system includes pre-operative planning and cutting guides by way of computer manufactured stereolithographic models for human facial transplantation. However, such a system uses standard off-the-shelf vendor systems and does not include necessary features to mitigate the increased complexity of this particular procedure.

Additionally, known CAS paradigms for craniomaxillofacial surgery provide little capacity for intraoperative plan updates. This feature becomes especially important since, in some circumstances during the transplantation surgery, it may be necessary to revise and update the preoperative plans intraoperatively.

What is needed in the art, therefore, is a single, fully-integrated platform, providing a computer-assisted surgery solution customized for pre-operative planning, intraoperative navigation, and dynamic, instantaneous feedback, for example, in the form of biomechanical simulation and real-time cephalometrics, for facial transplantation that addresses common shortcomings of existing CAS systems and has the potential to improve outcomes across both the pediatric and adult-based patient population.

SUMMARY

In an embodiment, there is a computer-assisted surgical system. The system can include a donor sub-system and a recipient sub-system. The donor sub-system includes a first reference unit having a first trackable element, a fragment reference unit having a second trackable element, and a first detector configured to provide at least one of a first signal corresponding to a detected location of one or more of the first trackable element and the second trackable element. The recipient sub-system includes a second reference unit having a third trackable element, and a second detector configured to provide at least one of a second signal corresponding to a detected location of at least the third trackable element.

In another embodiment, there is a computer-assisted, transplantation method. The method can include attaching a first reference unit having a first trackable element to a first anatomical feature of a donor being, attaching a fragment reference unit having a second trackable element to a second anatomical feature of the donor, detecting a location of at least one of the first trackable element and the second trackable element with a first detector. The first detector may be configured to provide at least one of a first signal corresponding to the detected location of at least one of the first trackable element and the second trackable element. The method may further include accessing a first computer readable reconstruction of the donor anatomy. The first computer readable reconstruction includes a first orientation that is updated based on a physical location of at least one of the first trackable element and the second trackable element as detected by the first detector. The method may further include attaching a second reference unit having a third trackable element to an anatomical feature of a recipient being and detecting a location of the third trackable element with a second detector. The second detector may be configured to provide at least one of a second signal corresponding to a detected location of at least the third trackable element. The method may further include accessing a second computer readable reconstruction of the recipient anatomy. The second computer readable reconstruction may include a second orientation that is updated based on a physical location of the third trackable element detected by the second detector. The method may further include superimposing a first virtual donor fragment of the first computer readable reconstruction on the second computer readable reconstruction.

Additional advantages of the embodiments will be set forth in part in the description which follows, and in part will be understood from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIGS. 2A-2C provide a schematic overview of a surgical system.

FIGS. 2D-2G are graphical representations of some components and/or features of the surgical system of FIGS. 2A-2C.

FIG. 5A shows a donor's face-jaw-teeth alloflap in suboptimal position as compared to a recipient's cranium. FIG. 5B shows appropriate face-jaw-teeth positioning with immediate surgeon feedback and updated cephalometric data pertinent to a pre-clinical investigation. A surgeon may adjust the position of face-jaw-teeth segment upwards, downwards, forwards, or backwards based on this real-time cephalometric feedback, as this information helps to predict optimal form and function. For instance, placing the face-jaw-teeth segment forward may improve the patient's airway, but if moved too far forward, it may cause the patient to have a significant overjet (i.e. malocclusion) and abnormal appearance in a profile view.

FIG. 8A illustrates a donor face-jaw-teeth alloflap recovery, FIG. 8B shows a recipient preparation prior to transplant, and FIG. 8C illustrates a custom pre-bent fixation plate and palatal splint designed to achieve face-jaw-teeth alignment and skeletal inset.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. $-1$, $-2$, $-3$, $-10$, $-20$, $-30$, etc.

The following embodiments are described for illustrative purposes only with reference to the figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

Disclosed are embodiments of a computer-assisted surgery system that provides for large animal and human pre-operative planning, intraoperative navigation which includes trackable surgical cutting guides, and dynamic, real-time instantaneous feedback of cephalometric measurements/angles as needed for medical procedures, such as facial transplantation, and many other instances of craniomaxillofacial and orthognathic surgery. Such a system can be referred to as a computer-assisted planning and execution (C.A.P.E.) system and can be exploited in complex craniomaxillofacial surgery like Le Fort-based, face-jaw-teeth transplantation, for example, and any type of orthognathic surgical procedure affecting one's dental alignment, and can include cross-gender facial transplantation.

Figure 1:
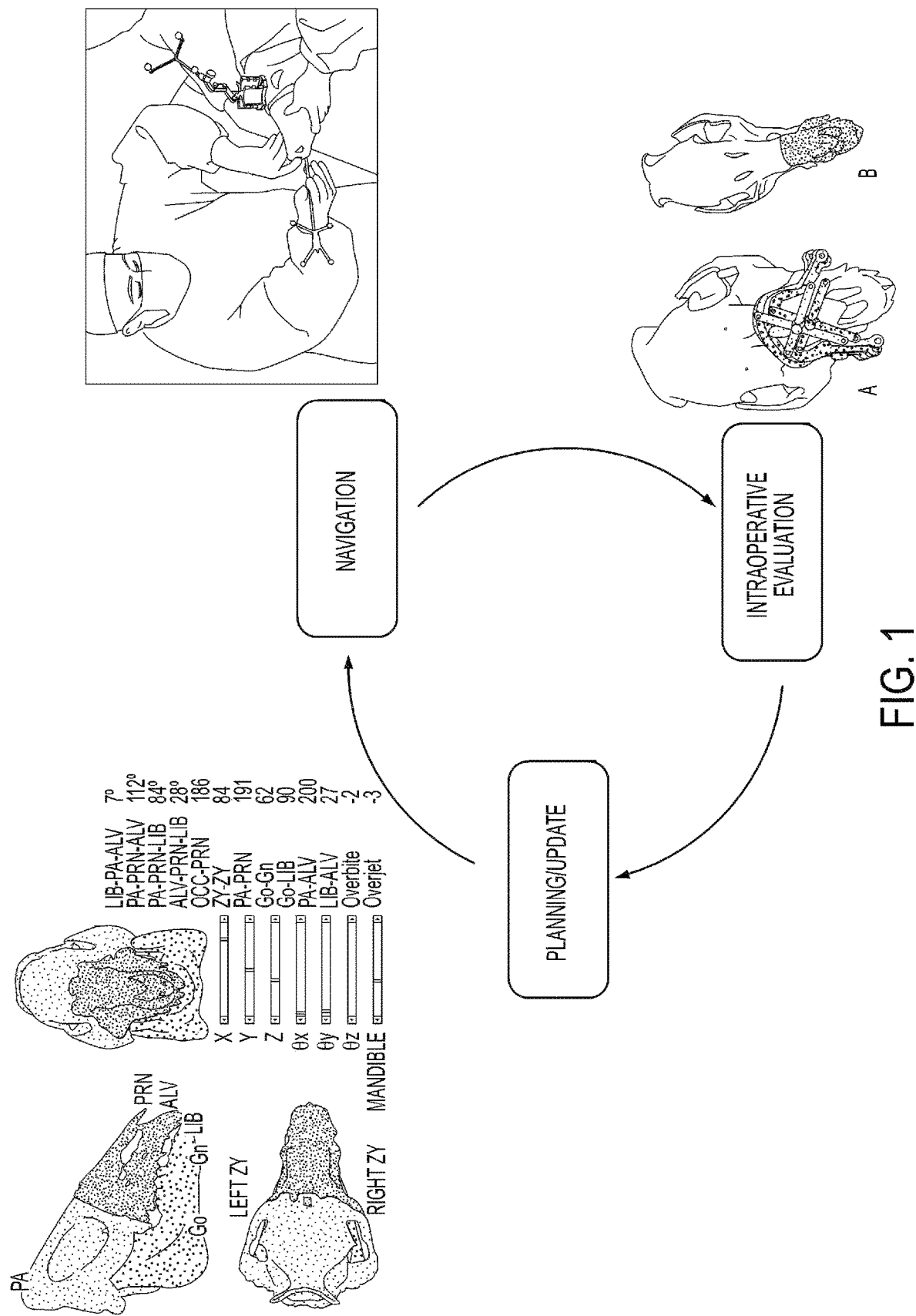
FIG. 1 is a flowchart of a surgical system and method that closes the loop between surgical planning, navigation, and enabling intraoperative updates to a surgical plan.
Figure 2A:
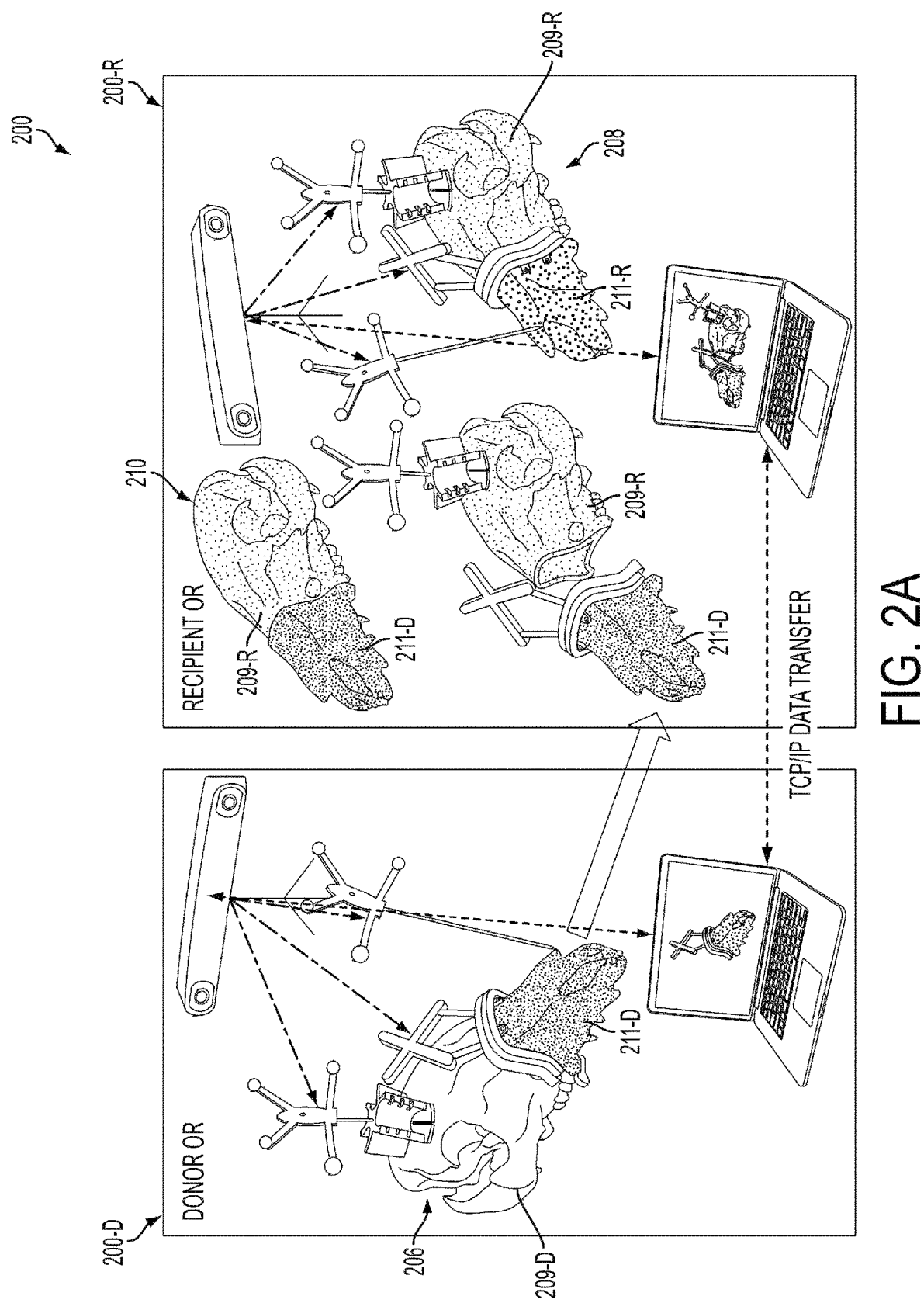
Figure 2B:
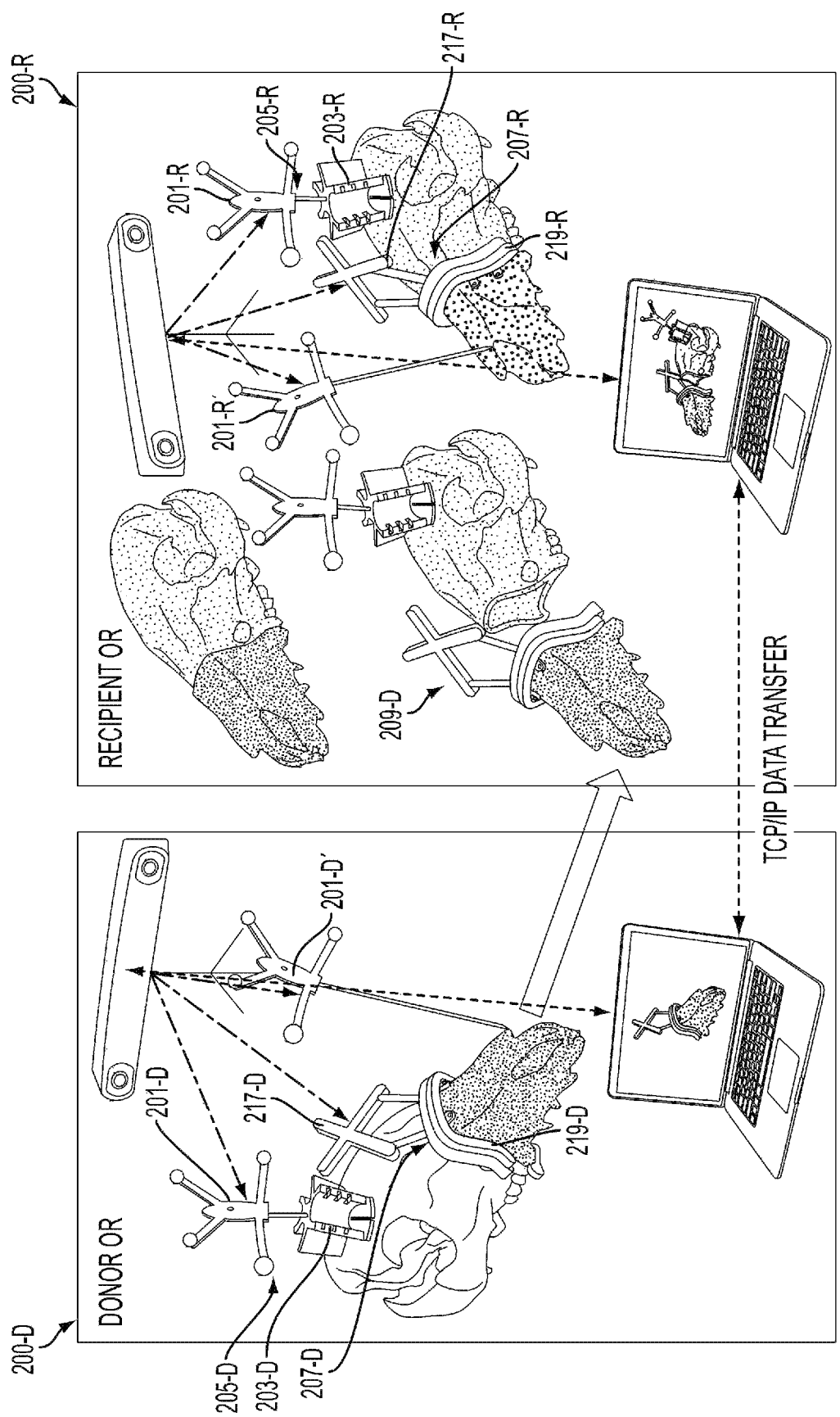

The fundamental paradigm for computer-assisted surgery (CAS) involves developing a surgical plan, registering the plan and instruments with respect to the patient, and carrying out the procedure according to the plan. Embodiments described herein include features for workstation modules within a CAS paradigm. As shown in FIG. 1, a surgical system of the embodiments can enable intraoperative evaluation of a surgical plan and can provide instrumentation for intraoperative plan updates/revisions when needed.

Embodiments can include a system with integrated planning and navigation modules, for example, a system for tracking donor and recipient surgical procedures simultaneously. In general, features of such a system can include: 1) two or more networked workstations concurrently used in planning and navigation of the two simultaneous surgeries for both donor and recipient irrespective of geographic proximity, 2) two or more trackers, such as electromagnetic trackers, optical trackers (e.g., Polaris, NDI Inc.), and the like, for tracking bone fragments, tools, and soft tissues, 3) one or more guides, reference kinematic markers, etc. as required for navigation. These features are described in further detail with respect to FIGS. 2A-2G.

Preoperative planning can include the following tasks: a) segmentation and volumetric reconstruction of the donor and recipient facial anatomy; b) planning for patient-specific cutting guide placement; c) cephalometric analysis and biomechanical simulation of the hybrid skeleton's occlusion and masticatory function, respectively; d) fabrication of the hybrid cutting guides enabling both geometric ("snap-on" fit) and optical navigation; e) 3D mapping the vascular system on both recipient and donor facial anatomy; and f) plan updates, if necessary, based on the feedback from the intraoperative module. As used herein, "snap-on fit" or "snap-on" or "snap on" are used to describe the way an item, such as a cutting guide, attaches to a pre-determined area. That is, the cutting guide actually "snaps-on" to a certain pre-determined area along the patient being's anatomy, such as the facial skeleton, and in all other areas it doesn't fit properly since size and width varies throughout significantly with many convexities and concavities.

Intraoperative tasks of embodiments described herein can generally include: 1) registering the preoperative model reconstructed from the CT data to donor and recipient anatomy; 2) visualizing (e.g., using information from the tracker, such as an electromagnetic tracker, optical tracker, and the like) the instruments and cutting guides to help the surgeon navigate; 3) verifying the placement of cutting guides, and performing real-time cephalometric and biomechanical simulation for occlusion analysis, if, for any reason, the osteotomy sites need to be revised; 4) dynamically tracking the attachment of the donor fragment to the recipient and providing quantitative and qualitative (e.g., visual) feedback to the surgeon for the purpose of improving final outcomes related to form (i.e., overall facial aesthetics) and function (i.e., mastication, occlusion relation, airway patency). Such a procedure is described in further detail below with respect to FIG. 3.

Preoperative Planning

In general, a method for performing a surgery includes a virtual surgical planning step that includes performing segmentation and 3D reconstruction of recipient and donor CT scans (e.g., Mimics 15.01, Materialise, Leuven Belgium). Virtual osteotomies can then be performed within the software to optimize the donor/recipient match. Patient-customized cutting guide templates can then be created (3-matic 7.01, Materialize, Leuven, Belgium). These templates can then be rapid-prototyped via an additive manufacturing modeling process, which can include, but is not limited to, stereolithography or 3D printing and the like. The surgical method and system for performing surgery are described in further detail below.

Figure 4B:
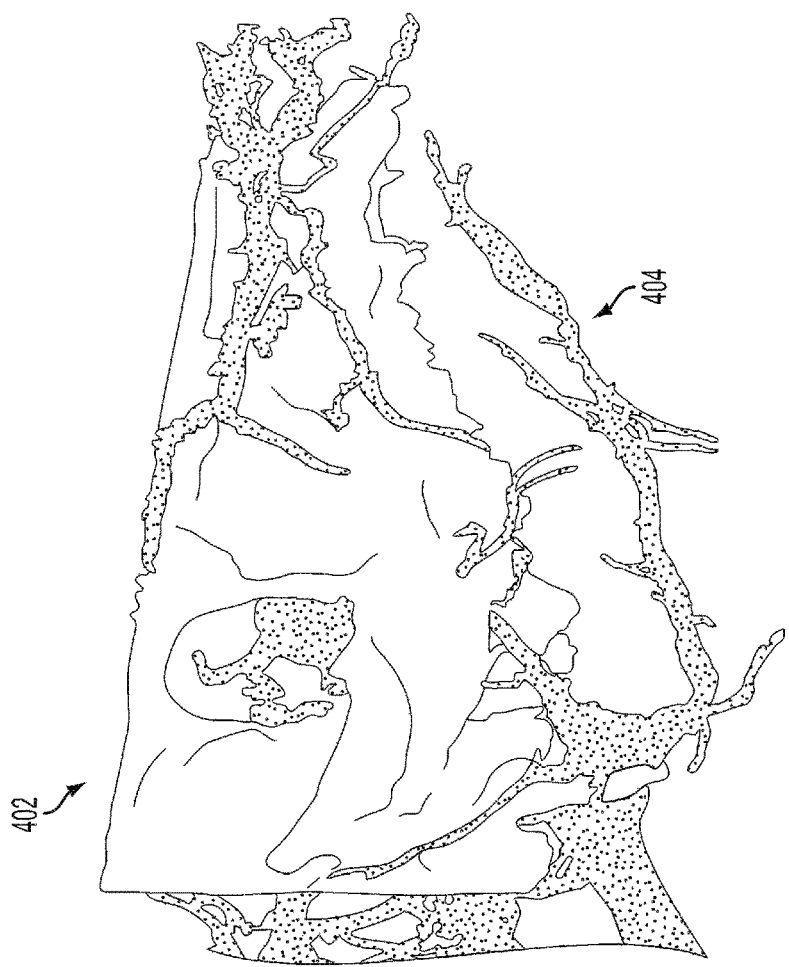
FIG. 4B shows a segmented arterial system of a craniomaxillofacial skeleton generated from CT angiography (CTA) data allowing 3D, intraoperative mapping.
Figure 4A:
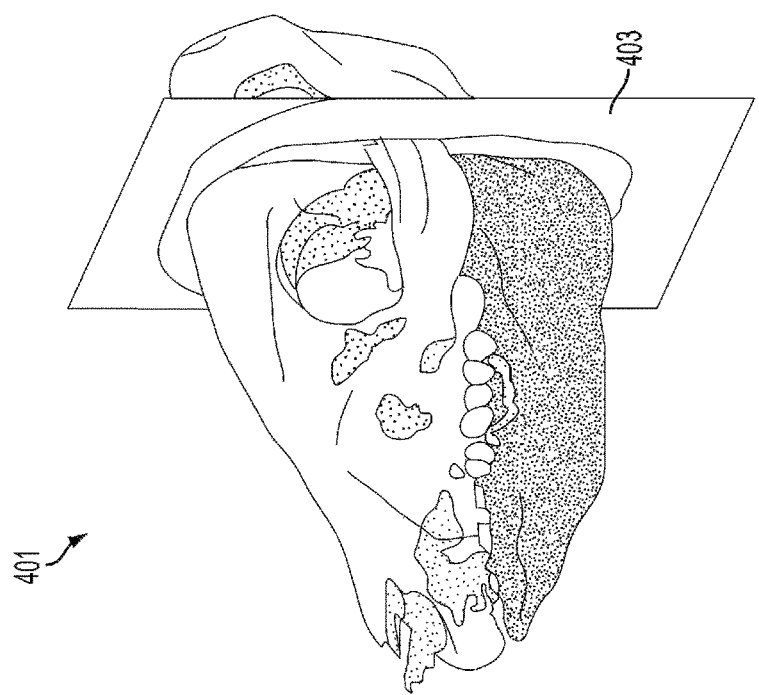
FIG. 4A is a CT-scan of reconstructed images of a size-mismatched facial skeleton generated from segmentation software utilized for pre-operative planning.
Figure 5A:
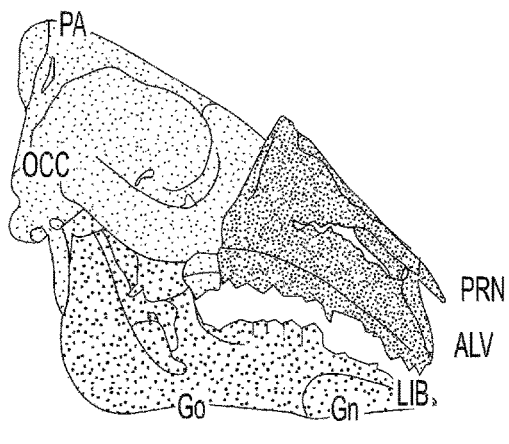
FIGS. 5A-5B show depictions of on-screen images provided by a surgical system, such as the surgical system of FIG. 2A displaying real-time, dynamic cephalometrics and pertinent measurements applicable to humans.
Figure 5A:
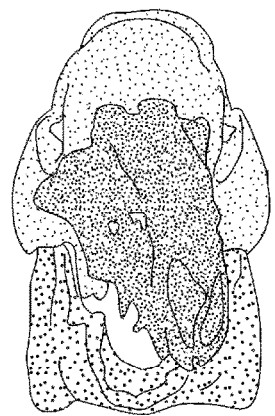
Figure 5A:
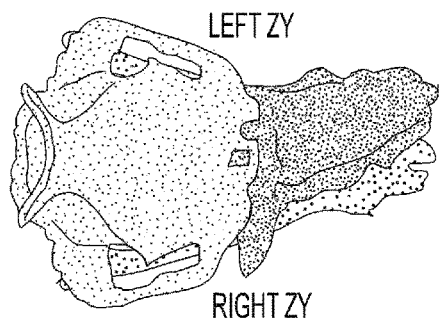
Figure 5B:
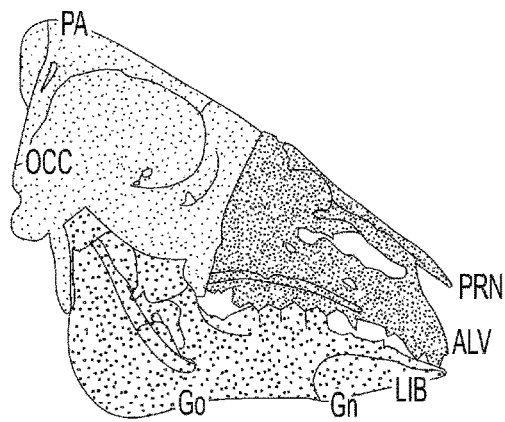
Figure 5B:
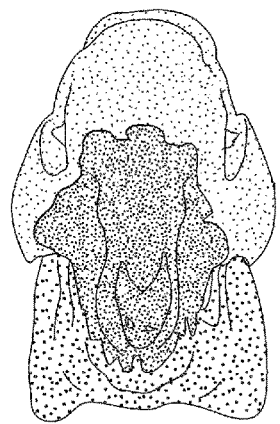
Figure 5B:
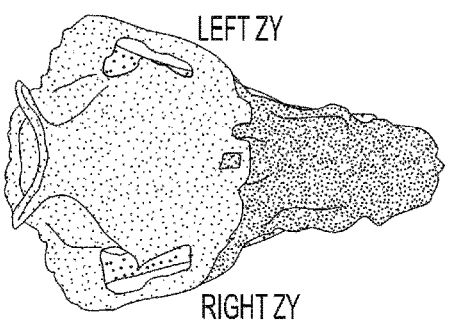

Referring to FIGS. 4A and 4B, during the initial planning stage, surgeons determine a virtual plan 401 based on the recipient's craniomaxillofacial deformity irrespective of the donor. From registered CT data, segmentation software generates volume data for specific key elements (e.g., the mandible, maxilla, and cranium) used for preoperative planning and visualization. The planning workstation automatically generates the expected cut geometry of the donor fragment 402 together with the recipient, thereby defining the predicted facial skeleton with accompanying hybrid occlusion. If available, blood vessels 404 are segmented from CT angiography scans as shown in FIG. 4B. That is, in an embodiment, nerves (via known nerve foramens) and vessels (both arteries and veins) can be localized to provide a full anatomical "road map" to the surgeons for a more precise, time-saving anatomical dissection with perhaps decreased blood loss and smaller incisions. The planning module can also perform static cephalometric analysis and evaluation of face-jaw-teeth harmony via biomechanical simulation on varying constructions of the hybrid donor and recipient jaws, such as that shown in FIGS. 5A-5B. Using this tool, the surgeon can evaluate different placements for the donor's face-jaw-teeth alloflap on the recipient's facial skeleton in relation to orbital volumes, airway patency, facial projection, and dental alignment. An automated cephalometric computation for the hybrid face indicates the validity of the planned surgery from both an aesthetic, functional and reconstructive standpoint based on various measurements of pertinent landmarks as shown, for example, in Tables 1A-B.

TABLE 1A

Pertinent landmarks for cephalometric analysis

| SYMBOL | NAME and DEFINITION |
|---|---|
| Go | Gonion: a point mid-way between points defining angles of the mandible |
| Gn | Gnathion: most convex point located at the symphysis of the mandible |
| ALV | Alveolare: mid-line of alveolar process of the upper jaw, at incisor - alveolar junction |
| LIB | Lower Incisor Base: midline of anterior border of alveolar process of mandible at the incisor-alveolar junction |
| PA | Parietale: most superior aspect of skull in the midline, (formed by nuchal crest of occipital bone and parietal bone) |
| PRN | Pronasale: bony landmark representing anterior limit of nasal bone |
| ZY | Zygion: most lateral point of malar bone |
| OCC | Occipital region: midpoint between the occipital condyles |

TABLE 1B

Cephalometric measurements and related units.

| Measure | ZY-ZY | PA-PRN | Go-Gn | Go-LIB | PA-ALV | LIB-ALV | Overbite | Overjet | OCC-PRN | LIB-PA-ALV | PA-PRN-ALV | PA-PRN-LIB | ALV-PRN-LIB |
|---|---|---|---|---|---|---|---|---|---|---|---|---|---|
| Units | mm | mm | mm | Mm | mm | mm | Mm | mm | mm | deg | deg | deg | deg |

To evaluate and predict cephalometric relationships both during planning and intra-operative environments, the system can use validated, translational landmarks between swine and human to thereby allow effective pre-clinical investigation. The cephalometric parameters defined by these landmarks can be automatically recalculated as the surgeon relocates the bone fragments using a workstation's graphical user interface.

Figure 6:
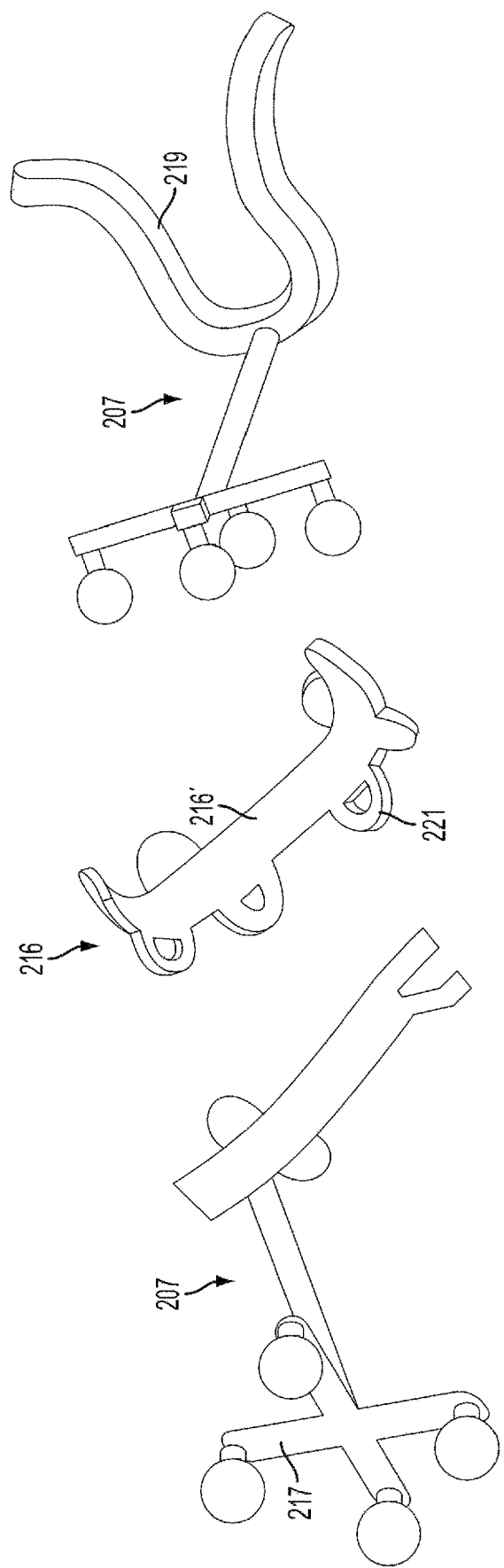
FIG. 6 shows some pre-bent fixation plates with screw holes designed virtually to accommodate the donor-to-recipient skeletal mismatch areas and matching navigational cutting guides of a surgical system, for example, the surgical system of FIGS. 2A-2C.
Figure 8A:
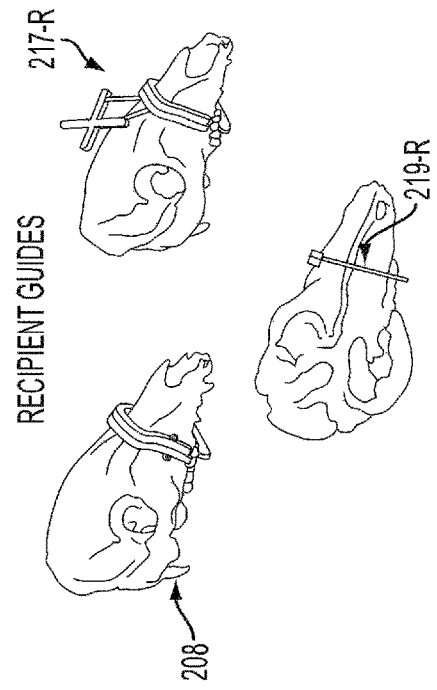
FIGS. 8A-8C are illustrations of cutting guides of the embodiments with navigational capabilities.
Figure 8B:
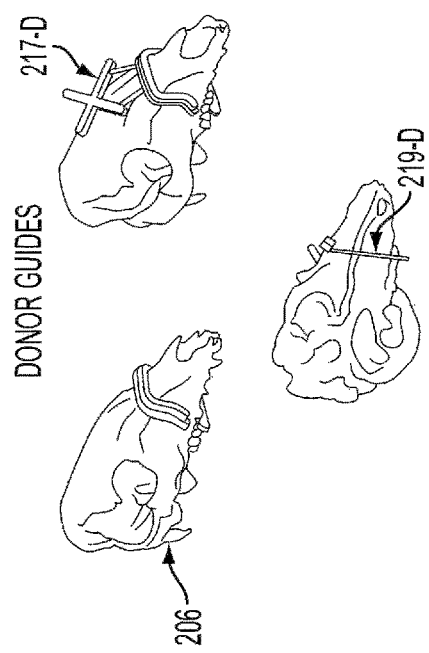
Figure 8C:
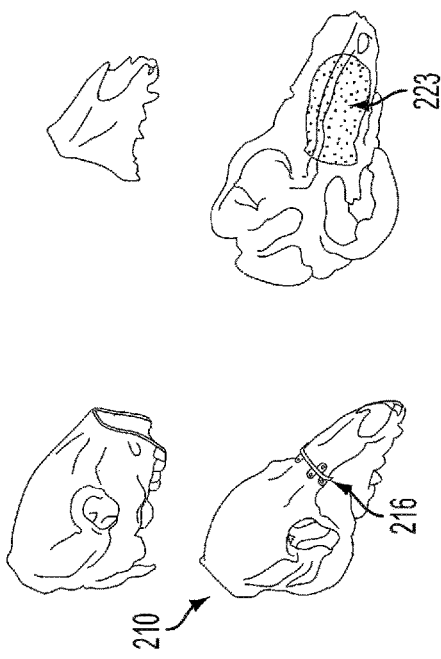

Preoperative planning can also involve fabrication of custom guides 207 (as shown in FIG. 6) and palatal splints 223 (as shown in FIG. 8C). Planned cut planes 403 (as shown in FIG. 4) can be used for defining the geometry of the cutting guides to thereby provide patient-specific cutting guides. These cutting guides can be designed according to the skeletal features through which the cutting plane intersects, such as an outer skeletal surface of a cross section defined by the cutting plane, and can be fabricated via stereolithography, or via any additive manufacture technology. In an embodiment, custom cutting guide templates can be separately designed and navigational registration elements can be added (Freeform Plus, 3D Systems, Rock Hill, S.C.). As discussed above, the surgical guides can be manufactured via additive manufacturing technology (AMT). The cutting guides can, therefore, be a 3D printing material such as a polymer, and can include an attachment surface 216 configured for attaching to a skeletal feature, and can have a "snap-on" fit to both donor and recipient. As described above, the attachment surface may include a contoured surface that corresponds to the contours of the skeletal feature within the planned cut planes. A navigation surface, such as a reference geometry 217 connected, built into, or attached to the guide structure directly or via attachment guides (not shown), enables dynamic intraoperative tracking of guides with respect to the patient's skeleton. Palatal splints ensure planned dento-skeletal alignment fixation following Le Fort-type facial transplants or any similar type of surgery. Fixation plates 216 can include a primary surface 216' and a plurality of fixation surfaces 221, such as eyelets, for screw placement to provide rigid immobilization at the irregular skeletal contour areas along various donor-to-recipient interfaces. Having pre-bent fixation plates decreases total operative times and helps to confirm accurate skeletal alignment by overcoming step-off deformities at bone-to-bone interfaces. Accordingly, at least one of the plurality of fixation surfaces can be located on one side of the primary surface and configured for attaching the fixation surface to a donor skeleton fragment, and at least one of another of the plurality of fixation surfaces is located on another side of the primary surface and configured for attaching the fixation surface to a recipient skeleton. The whole fixation plate or just portions of the fixation plate, such as the primary surface or fixation surfaces can be manufactured via additive manufacturing technology.

The cutting guide's navigation surface can include trackable objects, for example, on the reference geometry, such as infrared (IR) reflective coatings or IR emitters. For example, the trackable objects can include a plurality of integrated tracking spheres, each of which has an IR reflection surfaces.

Intraoperative Surgical Assistance

Figure 7B:
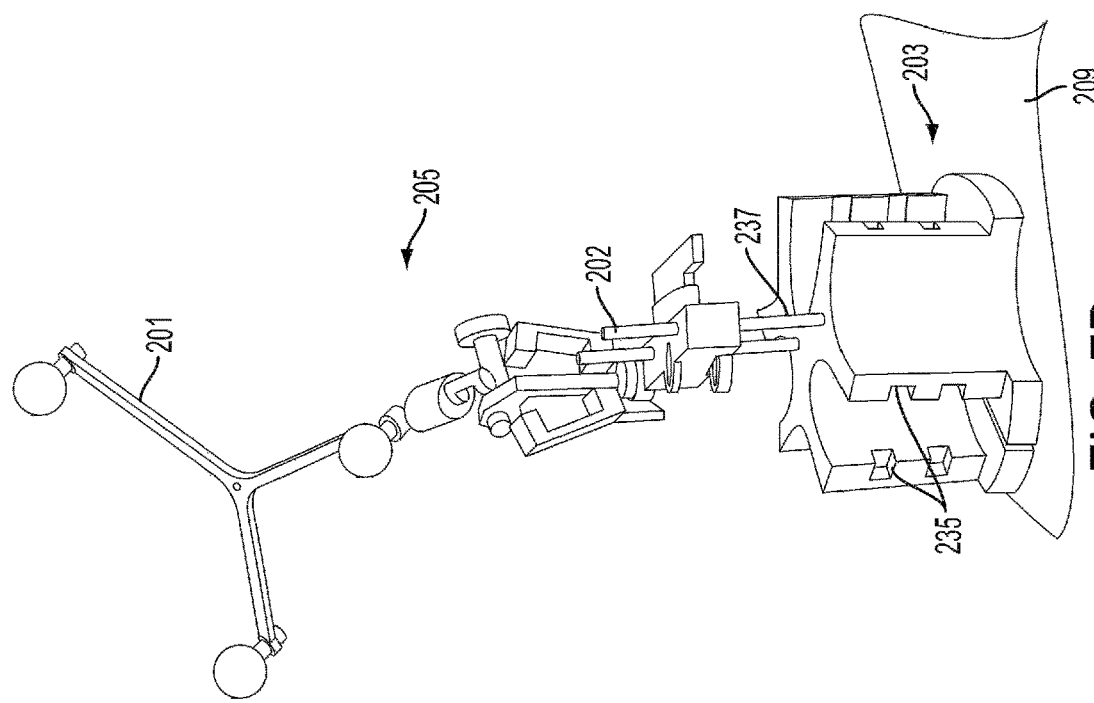
FIG. 7B shows a detachable rigid body with reflective markers attached to the reference body.
Figure 7A:
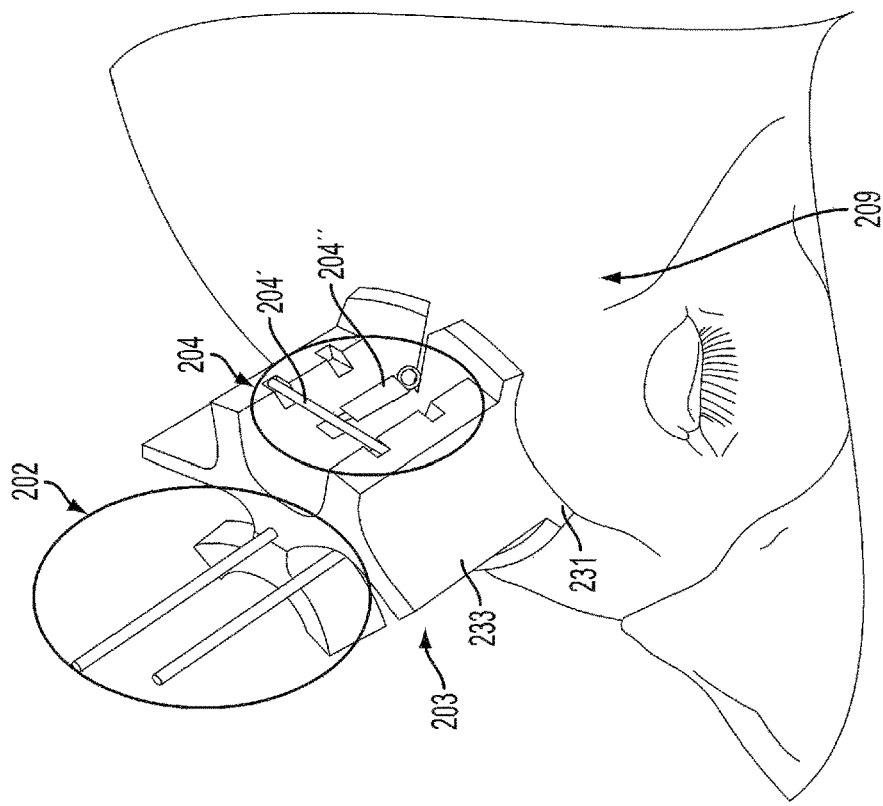
FIG. 7A shows a kinematic reference mount of an embodiment as it is affixed onto a donor's cranium with intermaxillary screws. A permanent suture (not visible) attaches stabilizers, such as springs and/or cross bars, which allow easy removal and replacement during surgery.

Individual navigation for both donor and recipient surgeries tracks the cutting guides with respect to planned positions. Surgeons can attach a reference unit, such as a kinematic reference mount to three intramedullary fixation (IMF) screws arranged in a triangular pattern on each the donor and recipient craniums as shown in FIG. 7A-7B. Accordingly, in an embodiment, there is a reference unit 205 for providing real-time surgical navigation assistance. The reference unit for providing real-time surgical navigation assistance can include a kinematic mount 203, at least one fixation rod 202, at least one support rod 204, and reference geometry 201. The kinematic mount 203 can include a base with a plurality of recesses defined by sidewalls 233, at least one pair of slots 235 defined by portions of the sidewalls, with each slot of the pair formed across the recess from the other slot, and at least one guide hole 237 extending through a length of the fixation plate. The at least one fixation rod 202 can extend through the at least one guide hole 237. An end of the at least one support rod can be configured for attaching to a skeleton of a being 209. The at least one support can be disposed in the pair of slots and can be configured to attach to the being. The reference geometry 201 can be attached to the at least one fixation rod.

The at least one support 204 can include at least one cross-bar 204' with ends that are configured for placement in the slots 235, and a spring 204" attached at one end to the at least one cross-bar 204' and attached at another end to the patient (e.g., a human-being). The spring attached at another end to the being can be attached via a suture (further described below). The reference unit 205 can further include a trackable object disposed on the reference geometry. The trackable object disposed on the reference geometry can include an IR reflective surface. The mount 203 can be made via additive manufacturing techniques and can therefore include a polymer. The at least one fixation rod can include a plurality of intramedullary fixation screws. The base can be configured for being detachably mounted on the skeleton of the being 209. The intramedullary fixation screws can be arranged in a triangular pattern. Accordingly the guide-holes can be configured in a triangular pattern on the base.

Accordingly, the mount design permits flexibility in the placement of the IMF screws so that no template is necessary. A spring 204" can attach to each IMF screw via suture threaded through, for example, the eyelets. These springs hold the cranial mount 203 in place and allow easy removal and replacement of the cranial mount (e.g. during positional changes required for bone cuts and soft tissue dissections). This may provide detachability and use of Intramaxillary fixation (IMF) screws for stable attachment The reference geometry 201 (e.g., which can be purchased from Brainlab, Westchester, Ill., USA) attached to the kinematic mount 203 provides a static coordinate frame attached to the patient. The surgeon can digitize three bony landmarks (e.g., the inferior aspect of the orbits and antero-superior maxilla) to define a rough registration between the environment and virtual models. For example, three, consistent points can be selected which can be quick to find, easy to reproduce on numerous occasions, and would remain constant irrespective of the user and his/her experience with the systems of the embodiments. The surgeon can thereby collect several point sets from exposed bone using a digitization tool and uses an iterative closest point registration technique to refine the registration. As shown in FIG. 8, once registered, the surgeon navigates the placement of the cutting guide 217 using the combination of "snap-on" geometric design and the tracking system coupled to visual feedback. This allows assessment of inaccuracies related to soft tissue interference, iatrogenic malpositioning, and anatomical changes since acquiring original CT scan data, and/or imperfections in cutting guide design or additive manufacturing process.

Self-drilling screws affix the cutting guide to the patient's skeleton to ensure osteotomies are performed along pre-defined planes, maximizing bony congruity. After dissecting the donor's maxillofacial fragment and preparing the recipient's anatomy, the surgical team transfers the facial alloflap. The system is configured to track the final three-dimensional placement of, for example, the Le Fort-based alloflap providing real-time visualization such as that shown in FIG. 5A-5B. This provides real-time visualization of important structures such as new orbital volumes (vertical limit of inset), airway patency (posterior horizontal limit of inset), and facial projection (anterior horizontal limit of inset). Once confirmed, the surgeon fixates the donor alloflap to the recipient following conventional techniques with plates and screws.

Accordingly, returning to FIGS. 2A-2G, there is a system 200 for tracking donor and recipient surgical procedures simultaneously. The system can include a donor sub-system 200-D, a recipient sub-system 200-R and a communications link (indicated by the horizontal dotted-line) such as a communication link that provides TCP/IP data transfer between the donor and recipient sub-systems. The donor sub-system can include a first computer workstation 215-D, a first cranial reference module 205-D, a first cutting guide 207-D for attaching to a preselected location of a donor skeleton 206, a first fragment reference module 201-D', and a first tracker 213-D. The first cutting guide 207-D can include an attachment surface 219-R configured for attaching to a skeletal feature, and a navigation surface 217-D connected to the attachment surface and comprising a trackable reference geometry. The first tracker 213-D may be configured to be in communication with the first computer workstation, for example, via a communications link. The first tracker can be configured to track, for example via IR optical tracking, a location of a portion of the first cranial reference module, a portion of the first cutting guide and a portion of the first fragment reference module. The recipient sub-system 200-R can include a second computer workstation 215-R, a second cranial reference module 205-R, and a second tracker 213-R. The second tracker 213-R can be configured to be in communication with the second computer workstation, for example, via a communications link. The second tracker can be configured to track, for example, via IR optical tracking, a location of a portion of the second cranial reference module. The communications link can connect the first computer workstation and the second computer workstation such that the first computer workstation and second computer workstation are able to communicate.

The recipient sub-system 200-R can further include a second fragment reference unit 201-R. The second tracker 213-R can further be configured to track a location of a portion of the second fragment unit.

The recipient sub-system 200-R can further include a second cutting guide 219-R for attaching to a preselected location of a recipient skeleton 208. The second tracker 213-R can further be configured to track a location of a portion of the second cutting guide.

Additionally, when a surgeon has removed the donor skeletal fragment from the donor, it can then be transferred for attachment onto the recipient. Accordingly, the second tracker 213-R can be further configured to track a location of a portion of the first cutting guide 207-D so that it can be matched relative a position of the second cranial reference module 205-R.

The first cranial reference unit, the second cranial reference unit, or both the first and second cranial reference units can include a kinematic mount 205 as described above.

Figure 3:
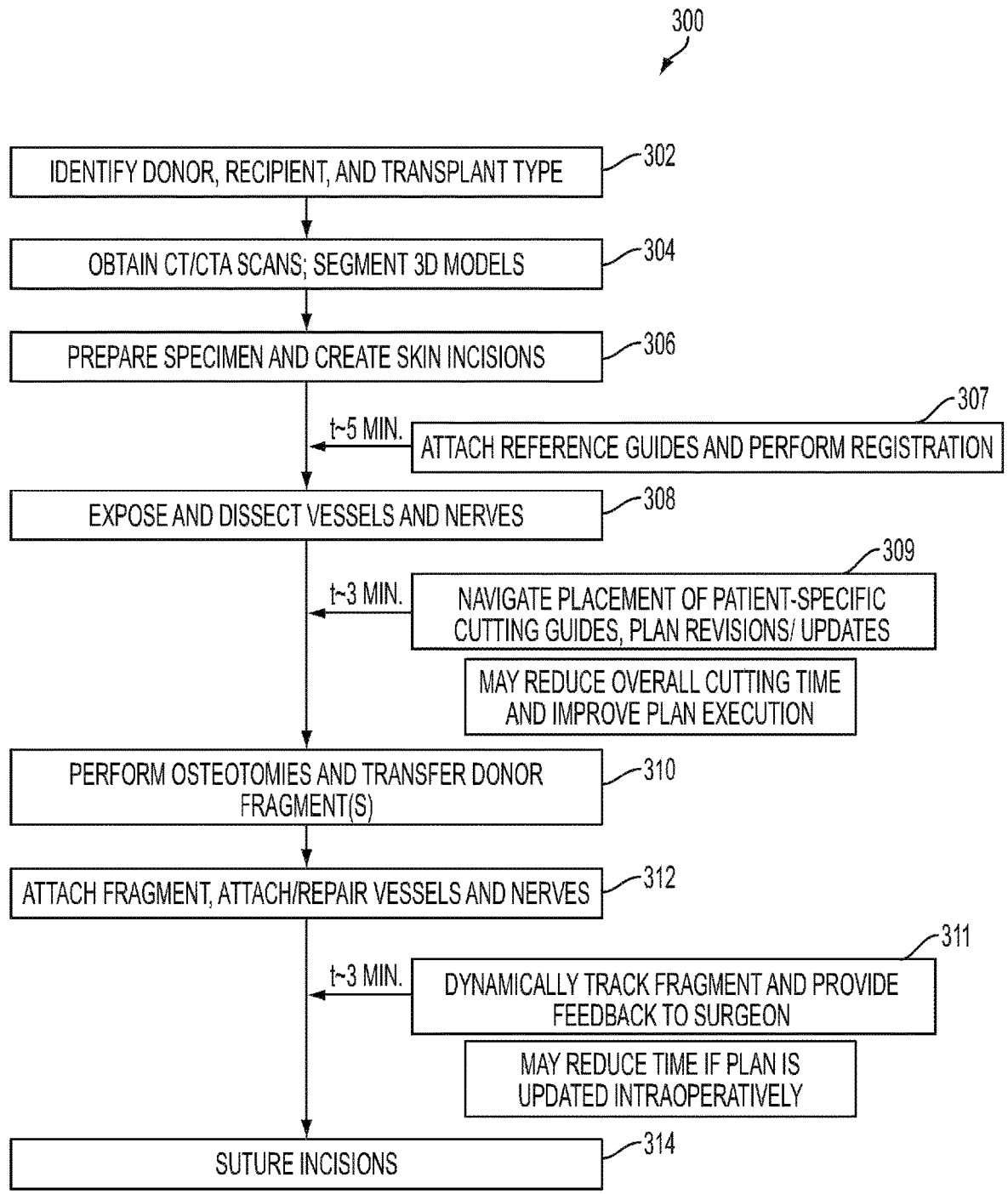
FIG. 3 is a flow chart depicting a procedure associated with use of the surgical system, for example, the surgical system of FIGS. 2A-2C.

Using the system of FIGS. 2A-2G, it is possible to execute a surgical method, such as the surgical method described in FIG. 3. For example, in step 302 a donor, recipient and transplant type are identified. CT/CTA scans of both the donor and recipient are collected and 3D models are created in step 304. The donor and recipients are prepared for surgery with the creation of skin incisions in step 306. The method continues at 307 with attachment of reference guides and performing registration. For example, a first cranial reference unit can be attached to a donor skeleton, a first fragment reference unit can also be attached to the donor skeleton at a location that is different that of the first cranial reference unit. The locations of the first cranial reference unit and the first fragment reference unit can be tracked with a first tracker. 3D reconstructions of the donor skeleton can be constructed showing a first virtual cranial reference unit and first virtual fragment reference unit superimposed on the first 3D reconstruction at locations that correspond to relative positions of the first cranial reference unit and the first fragment reference unit.

A second cranial reference unit can be attached to a recipient skeleton. A second location of the second cranial reference unit can be tracked with a second tracker. A second 3D reconstruction of the recipient skeleton can be created with a second virtual cranial reference unit superimposed on the second 3D reconstruction at a location that corresponds to a location of the second cranial reference unit. At 308, vessels and nerves are dissected and exposed. At this stage, navigation of the patient-specific cutting guides can occur, with plan revision and updates provided periodically. For example, a first cutting guide, such as a patient-specific cutting guide according to the descriptions provided above, can be attached onto the donor skeleton at a preselected location such as that corresponding to a planned cut-plane. The location of the first cutting guide can be tracked with the first tracker. A first virtual cutting guide can be superimposed on the first 3D reconstruction at a location that corresponds to a location of the first cutting guide relative to the location of the first cranial reference unit or the location of the first fragment reference unit.

A first virtual fragment can be formed by segmenting the 3D reconstruction of the donor skeleton at a location adjacent to the first virtual cutting guide. The first virtual fragment can be superimposed on the second 3D reconstruction of the recipient skeleton.

At step 310, a surgeon can perform an osteotomy on the donor skeleton to remove the first fragment but cutting the skeleton along a cutting path defined by the first cutting guide. Upon transferring the removed skeletal fragment from the donor, the first cutting guide can be tracked, by the second tracker, for example, when the fragment is brought near the recipient for attachment. The surgeon can then navigate placement of the cutting guide as it is dynamically tracked at step 311, and will receive feedback from the system such as by referring to a first virtual fragment that is superimposed on the second 3D reconstruction to form a hybrid 3D reconstruction. At step 312, the first fragment can then be attached to the recipient skeleton via known surgical methods and the incisions can be sutured in step 314.

The step of superimposing the first virtual fragment on the second 3D reconstruction of the recipient skeleton can include performing an automated cephalometric computation for the hybrid reconstruction. In fact, the step of superimposing the first virtual fragment on the second 3D reconstruction can include providing a communications link between a first workstation on which the first 3D reconstruction is displayed and a second workstation on which the second 3D reconstruction is displayed, and initiating a data transfer protocol that causes the first workstation and the second workstation to send electronic signals through the communications link.

Surgical methods of the embodiments described above can also include attaching a second cutting guide at a preselected location on the recipient skeleton. The second cutting guide can also include features of the cutting guide described above.

For the surgical methods of embodiments described herein the donor skeleton can include a male skeleton or a female skeleton and the recipient skeleton can include a female skeleton. Alternatively, the donor skeleton can include a male or female skeleton and the recipient skeleton can include a male skeleton.

Surgical methods of the embodiments can further include steps for assessing a size-mismatch between the donor skeleton and the recipient skeleton by measuring a dorsal maxillary interface between the first fragment and recipient skeleton. In an embodiment, the surgical method can include selecting a location of the first fragment onto the recipient skeleton that minimizes dorsal step-off deformity at the area of osteosynthesis. In an embodiment, the first cutting guide, the second cutting guide, or both the first cutting guide and the second guide may be or include concentric cutting guides.

Surgical methods of embodiments can further include mapping the vascular system on the facial anatomy of both the recipient and the donor and superimposing corresponding virtual representations of the vascular system and the facial anatomy onto the first 3D representation, such as shown in FIG. 4B

Surgical methods of embodiments can include a method for registration of a preoperative model, for example a model reconstructed from CT data, to donor and recipient anatomy. Such a method can include: creating a plurality of indentations on the donor skeleton, creating a plurality of virtual markers on the first 3D reconstruction of the donor skeleton corresponding to the locations of the indentations on the donor skeleton, placing a trackable object on at least one of the plurality of indentations, and determining whether a subsequent location of the virtual markers is within a predetermined tolerance relative to an actual subsequent location of the indentations.

EXAMPLES

Example 1

Figure 9A:
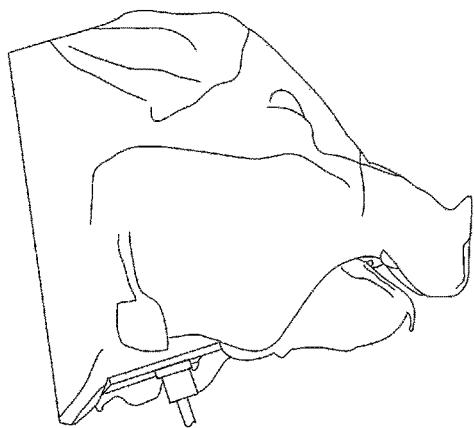
FIGS. 9A-9D are renderings showing exemplary surgical results.
Figure 9B:
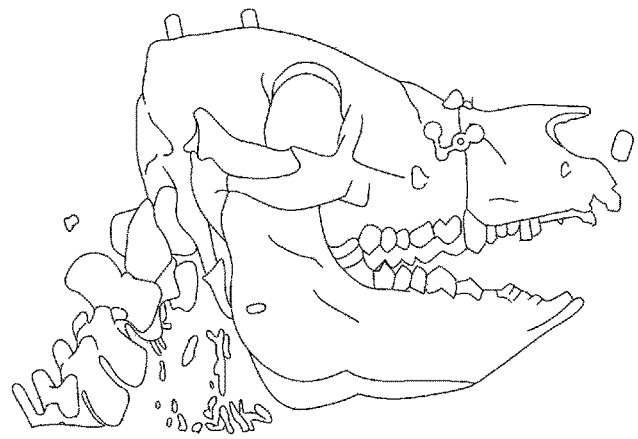
Figure 9C:
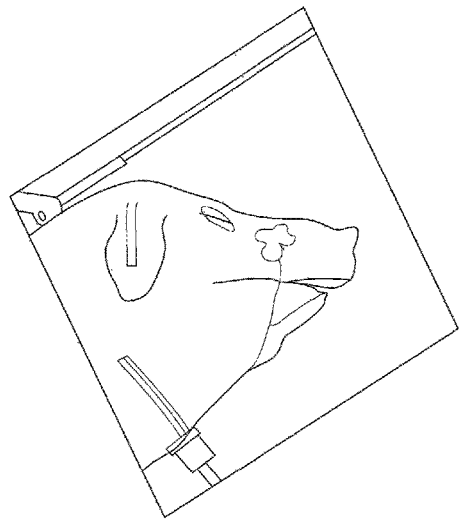
Figure 9D:
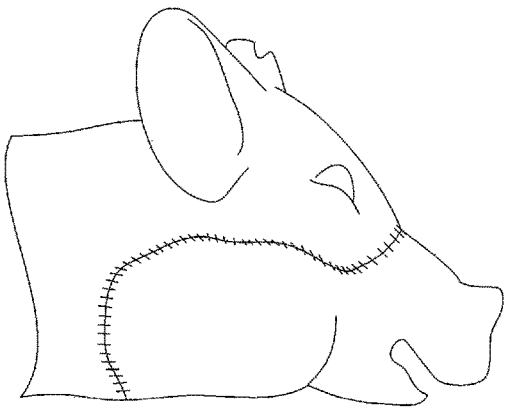

Live transplant surgeries (n=2) between four size-mismatched swine investigated whether or not an embodiment could actually assist a surgical team in planning and executing a desired surgical plan. As shown in FIGS. 9A-9B, the first live surgery confirmed the proposed utility of overcoming soft and hard tissue discrepancies related to function and aesthetics. The final occlusal plane within the first recipient was ideal and consistent with the virtual plan as seen on lateral cephalogram as shown in FIG. 10C. Pre-operative functional predictions of donor-to-recipient occlusion were realized based on cephalometric analyses as shown in FIG. 9C performed both before and after surgery. Soft tissue inconsistencies of the larger-to-smaller swine scenario were also reduced following the predicted movements of face, jaw and teeth as shown in FIG. 10D.

The second live surgery showed improved success as compared to its predecessor due to surgeon familiarity and technology modifications. System improvements and growing comfort of the surgeons led to reduced operative times for both donor and recipient surgeries. Overall the surgical time reduced from over 14 hours to less than 8 hours due to improved surgical workflow and increased comfort with a system of an embodiment.

Based on the results obtained in the live and plastic bone surgeries, the functions associated with setting up a system of an embodiment (attaching references, performing registration, attaching cutting guides) adds about 11 minutes to the total length of surgery.

Figure 10B:
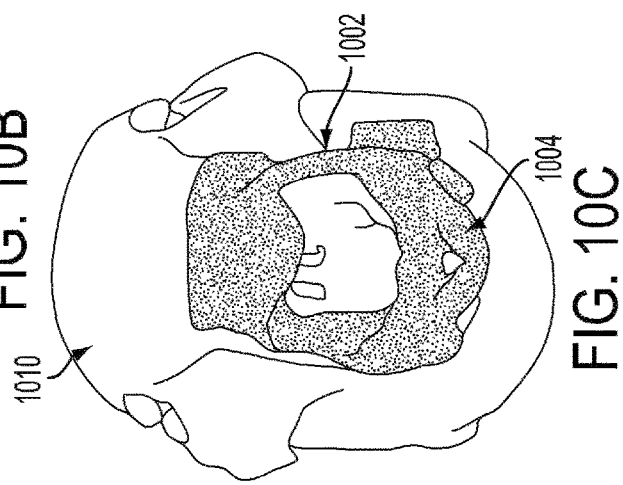
FIGS. 10A-10C are a top-view (bird's eye view), a left-sided profile view, and a frontal view, respectively, of images displayed by an imaging system of a surgical system. The images depict a recipient skeleton and include real-time assessment of planned versus actual face-jaw-teeth positions.
Figure 10C:
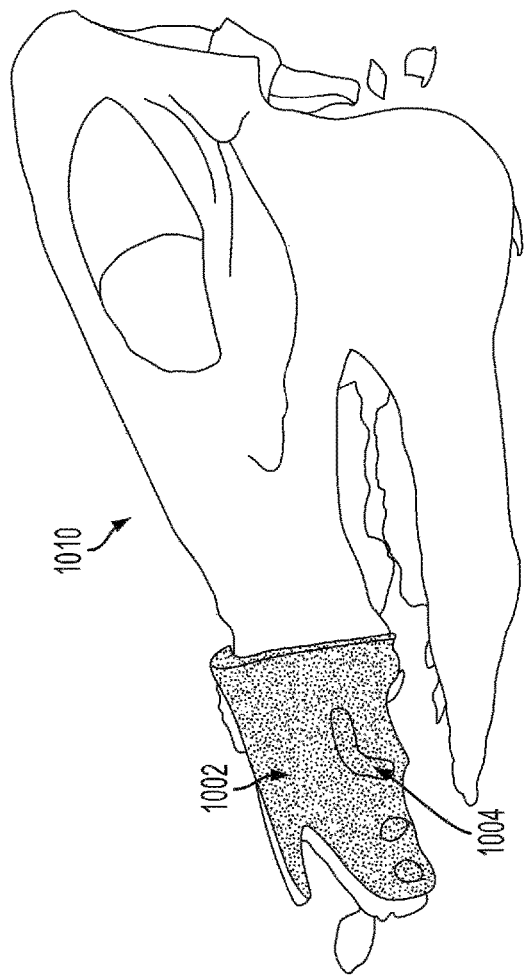
Figure 10A:
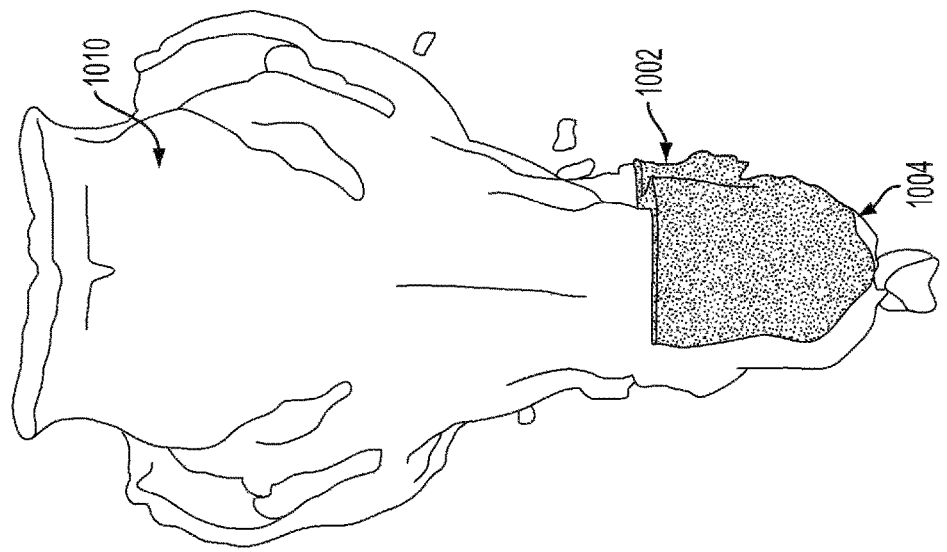
Figure 11A:
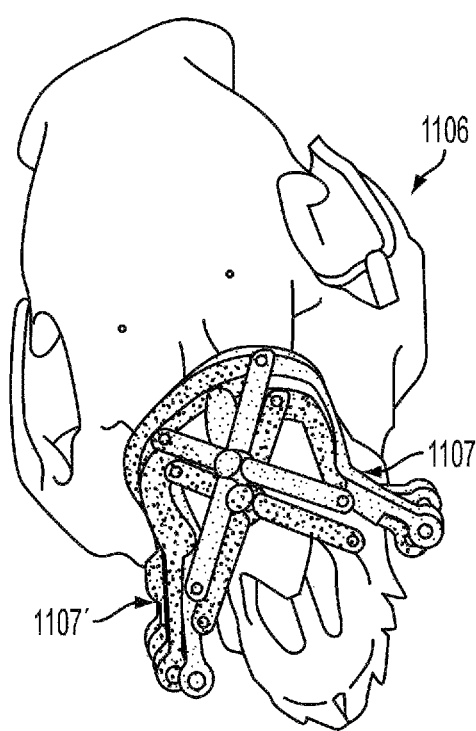
FIGS. 11A-11B are "on screen" images displayed by an imaging sub-system of a surgical system. The images depict an ideal location of a cutting guide versus an actual position and an actual inset position of a donor alloflap for aesthetic, dental, and skeletal relation in size-mismatched donors due to anterior translation of cutting guide.
Figure 11B:
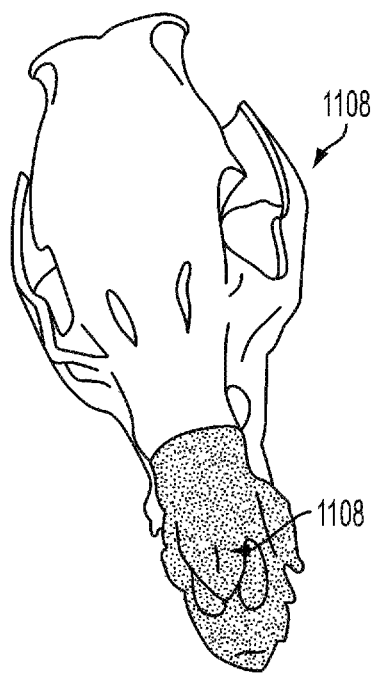
Figure 12A:
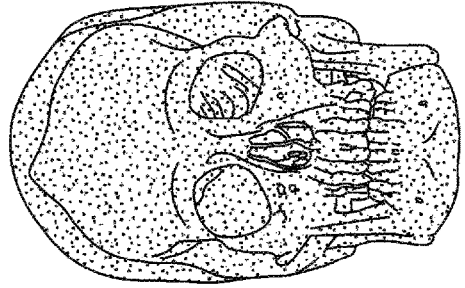
FIGS. 12A-H illustrate a virtual osteotomy and planned cut plane placement on virtual representations of a skeletal feature.
Figure 12B:
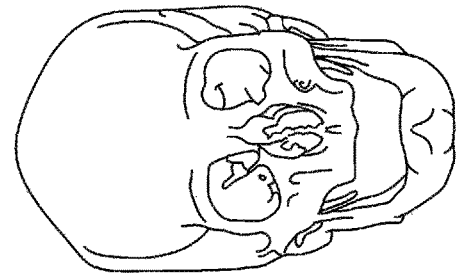
Figure 12C:
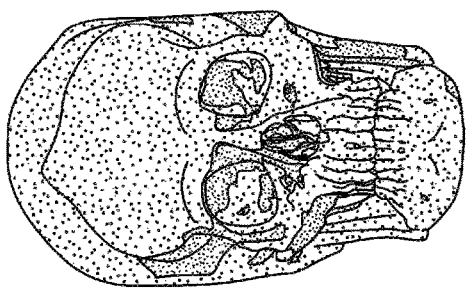
Figure 12D:
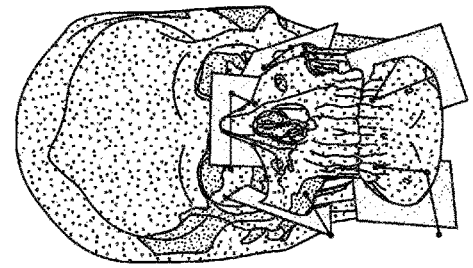
Figure 12E:
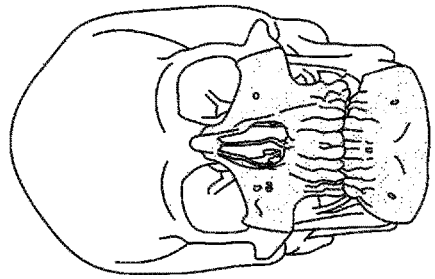
Figure 12F:
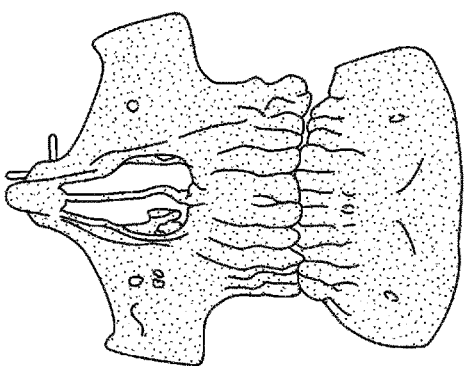
Figure 12G:
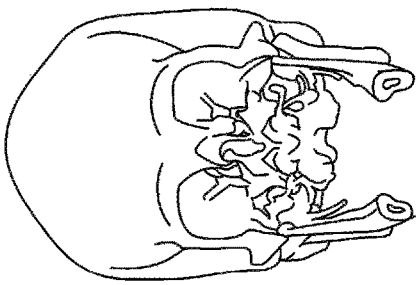
Figure 12H:
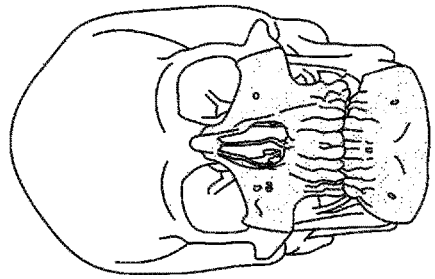
Figure 13A:
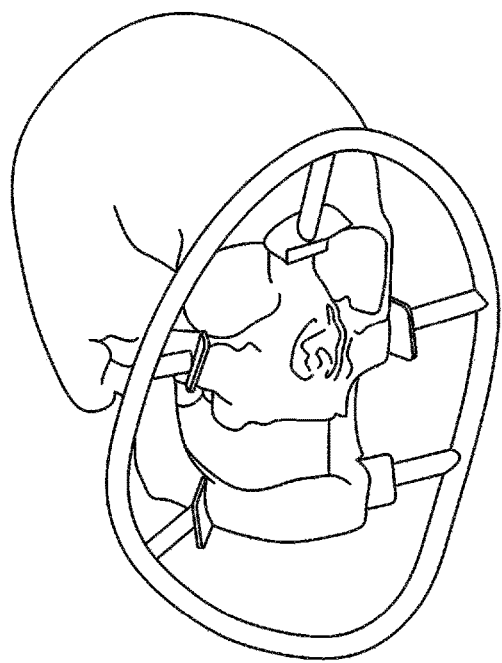
FIGS. 13A-13D illustrate a virtual placement of a cutting guide alongside (FIGS. 13A-13B) and illustrated representations of an actual placement (FIGS. 13C-13D).
Figure 13B:
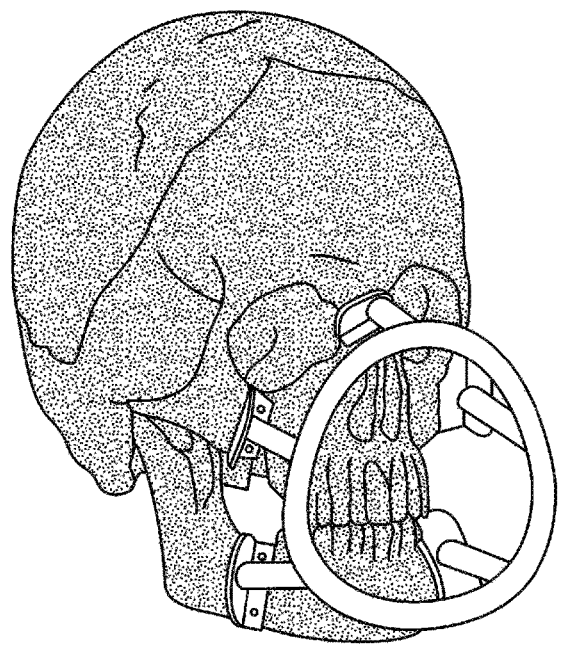
Figure 13C:
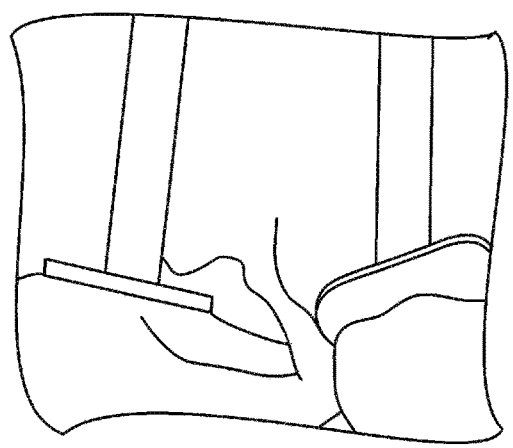
Figure 13D:
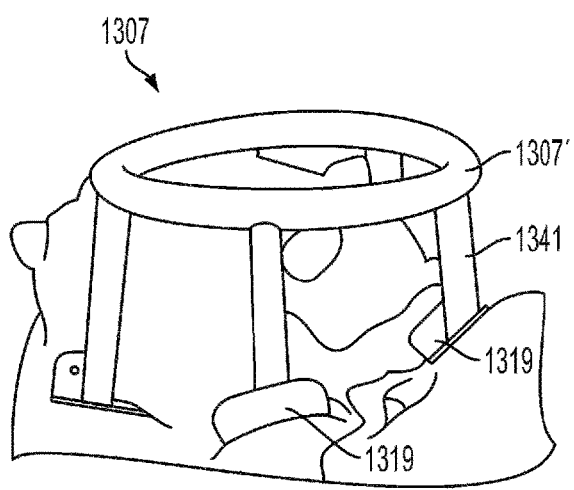

The system also recorded information, such as rendering information which can be stored in a storage medium of a workstation, relating the donor fragment 1002 to the recipient 1010 qualitatively as shown by color mismatch 1004, which matched the post-operative CT data as shown in FIG. 10. The recipient cutting guide 1107' was not placed as planned 1107 due to an unexpected collision between the cranial reference mount and the recipient cutting guide as shown in FIGS. 11A-11B. In this case, there was anterior translation of the cutting guide (toward the tip of the swine's snout) by approximately 4 cm.

Overall, the donor 1106 and recipient craniums (n=4) 1108 were registered successfully to the reference bodies for both live surgeries. The model to patient registration error across the surgeries was 0.6 (+/−0.24) mm. The cutting guide designs of the embodiments proved highly useful in carrying out the planned bone cuts, which compensated for size-mismatch discrepancies between donor and recipient. Marking spheres fixated to the guides allowed real-time movement tracking and "on-table" alloflap superimposition onto the recipient thereby allowing visualization of the final transplant result.

Example 2

Female and male donor heads (n=2), double-jaw, Le Fort III-based alloflaps were harvested using handheld osteotomes, a reciprocating saw, and a fine vibrating reciprocating saw. Both osteocutaneous alloflaps were harvested using a double-jaw, Le Fort III-based design (a craniomaxillofacial disjunction), with preservation of the pterygoid plates, incorporating all of the midfacial skeleton, complete anterior mandible with dentition, and overlying soft tissue components necessary for ideal reconstruction.

Prior to transplantation, both scenarios were completed virtually given the gender-specific challenges to allow custom guide fabrication as shown in panels A-H of FIG. 12. Once assimilated, the donor orthognathic two-jaw units were placed into external maxilla-mandibular fixation (MMF) using screw-fixated cutting guides to retain occlusal relationships during the mock transplants as shown in panels A-D of FIG. 13.

Figure 14A:
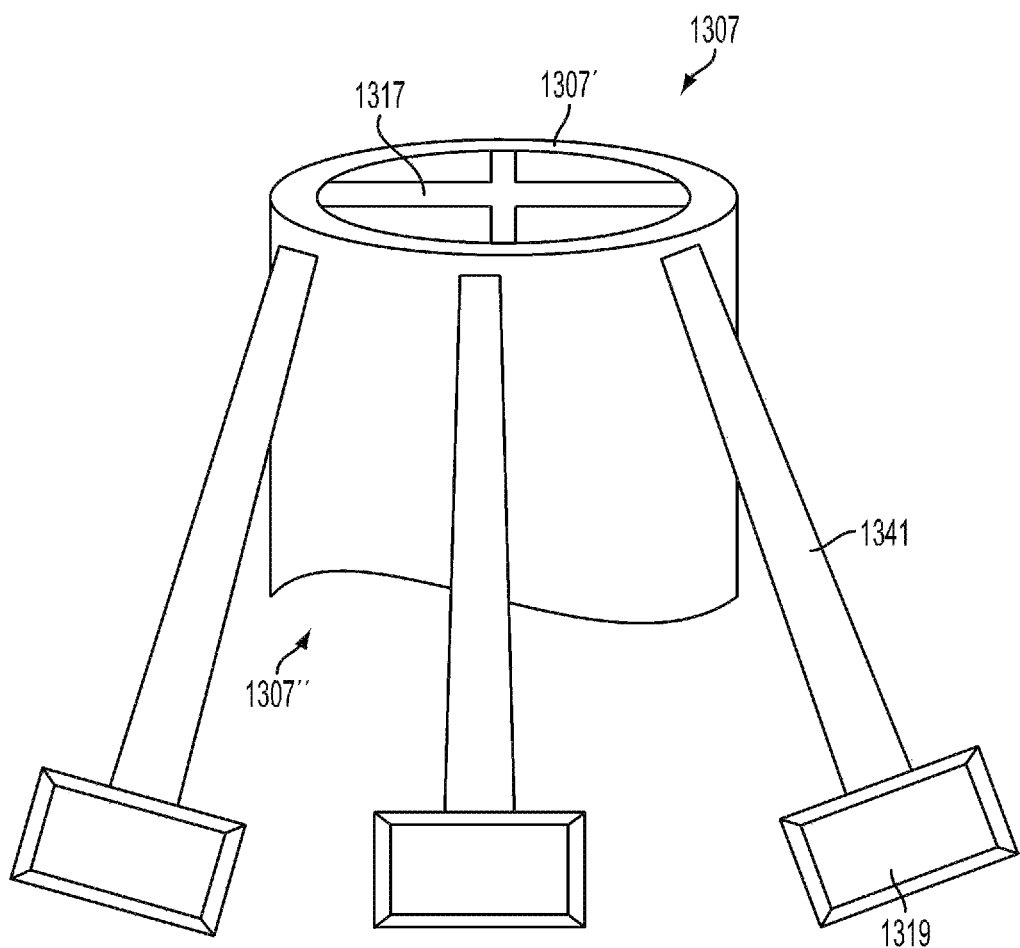
FIG. 14A illustrates a perspective view of a variation of a cutting guide, for example, a variation of the cutting guide of FIG. 13.
Figure 14B:
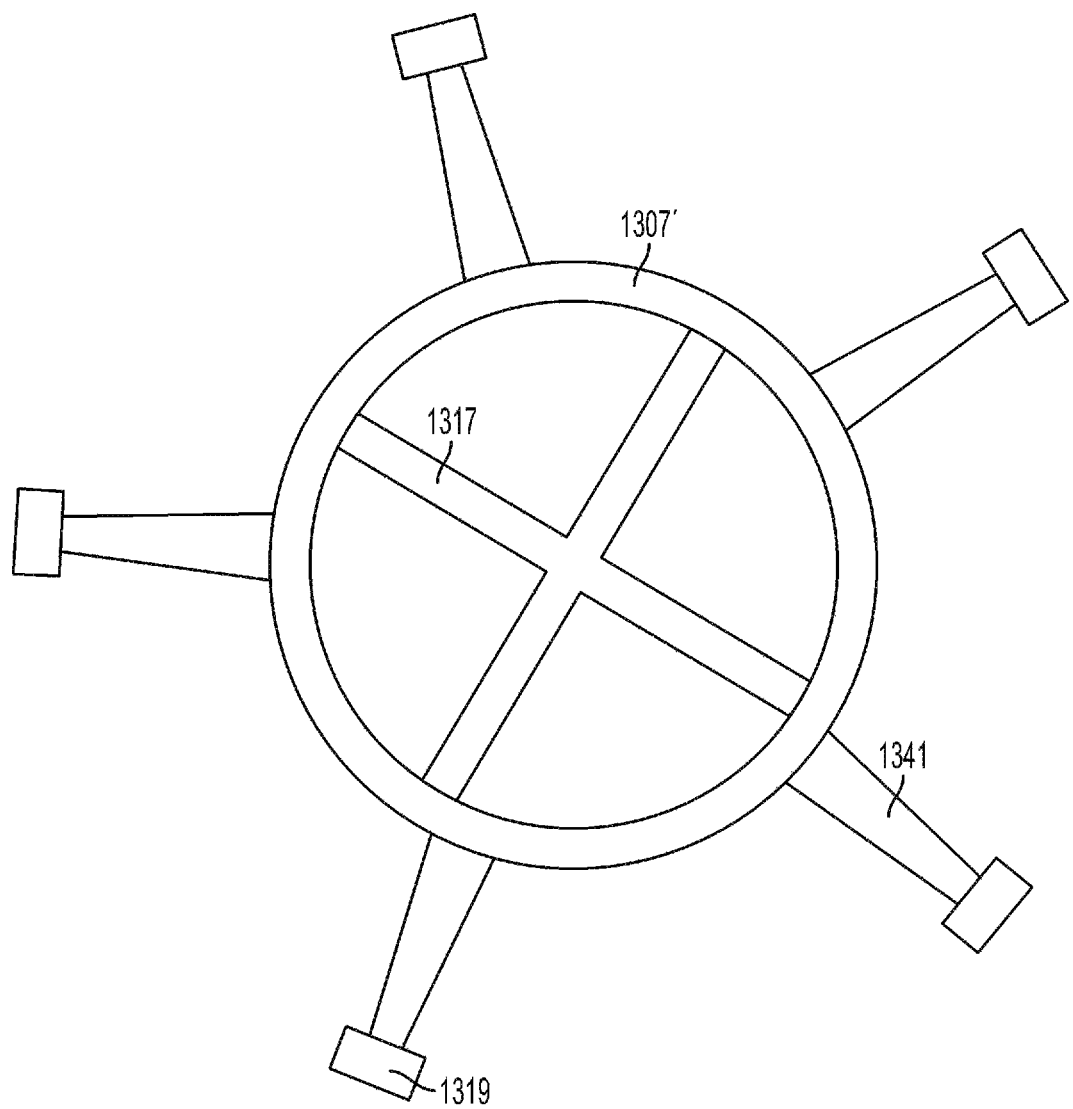
FIG. 14B illustrates a top view of a variation of a cutting guide, for example, a variation of the cutting guide of FIG. 13.

As shown in FIGS. 13, 14A-14B, an embodiment of a cutting guide 1307 can include a frame 1307' with at least one attachment surface 1319, for example 1 to 6 attachment surfaces, configured for attaching the cutting guide to a skeletal feature. The cutting guide can include a navigation surface 1317 (not shown in FIG. 13) connected to the frame. The navigation surface can include a reference geometry that can be tracked by a tracker, for example, via IR optical tracking. The at least one attachment surface 1319 can include a contoured surface corresponding to contours of portions of the skeletal feature, for example, such as the contours of a skeletal feature that intersect a planned-cut plane as indicated by 1319' in FIG. 12. The at least one attachment surface 1319 can be detachably connected to a skeletal feature. The at least one attachment surface 1319 can be detachably connected to an attachment guide 1341. The attachment guide 1341 can be detachably connected to a portion of the frame 1307'. For example, attachment guides 1341 can be detachably connected via slots integrated into frame 1307', or held in place against frame 1307 with screws or the like. In another embodiment, attachment guides 1341 are formed as portions of frame 1307' but can be removed. The frame can have a ring-like shape (as shown in FIG. 13) or can have a cylinder-like shape (as shown in FIG. 14A). Frame 1307' having a cylinder like shape can have a bottom surface 1307" that rests against a patient's soft tissue to provide support for the frame.

For example, during a surgical procedure, 3D reconstructions of portions of a donor skeleton are created. Planned cutting planes are selected and a cutting guide with attachment surfaces having a contoured surface corresponding to contours of portions of the skeletal feature, for example, such as the contours of a skeletal feature that intersect a planned-cut plane, is designed. The designed cutting guide is manufactured via, for example, an additive manufacturing process. The designed cutting guide with an integrated navigation surface is attached to the patient. For example, the cutting guide can be designed such that it has a snap-on fit over the skeletal feature, which can be further secured to the skeletal feature with set screws. A surgeon removes a donor skeletal fragment with the cutting guide attached to the fragment. The donor skeletal fragment is then attached to the recipient. As the donor skeletal fragment is attached to the recipient, the attachment surfaces are removed from the donor fragment. For example, each of the attachment guides 1341 with a corresponding attachment surface 1319 can be detached from the frame 1307'. As this occurs, a cylindrical shaped frame 1307' has a bottom surface 1307" that rests against the soft tissue of the patient to provide stability for the remaining portions of the cutting guide and to hold the navigation surface 1317' in place.

While the invention has been illustrated respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. For example, the embodiments described herein can be used for navigation and modeling for osteotomy guidance during double-jaw face transplantation, single-jaw maxillofacial transplantation, and any other neurosurgical, ENT/head and neck surgery, or oral maxillofacial surgical procedure alike.

Embodiments described herein can include platforms for preoperative planning and intraoperative predictions related to soft tissue-skeletal-dental alignment with real-time tracking of cutting guides for two mismatched jaws of varying width, height and projection. Additional safeguards, such as collection of confidence points, further enable intraoperative verification of the system accuracy. This, in addition to performing real-time plan verification via tracking and dynamic cephalometry, can considerably increase the robustness of the systems described herein. Moreover, systems of embodiments can include a modular system that allows additional functionality to be continually added.

Embodiments described herein can include an approach for resolving conflicts in case of position discrepancies between the placement of the guide and the guide position prompted by the navigation software. Such discrepancy may be due to either the guide (soft tissue interference, iatrogenic malpositioning, changes since the CT data was obtained or imperfections in cutting guide construction/printing), and/or the navigation system (e.g. registration error, or unintended movement of the kinematic markers). To resolve these source(s) of discrepancy, four indentations can be created on a bone fragment (confidence points) where a reference kinematic marker is attached. At any time during an operation, a surgeon can use a digitizer and compare the consistency of the reported coordinates of the indentations via navigation to their coordinates with respect to a virtual computer model.

Embodiments described herein can include a system that provides real-time dynamic cephalometrics and masticatory muscle biomechanical simulation for both planning and intraoperative guidance to ensure ideal outcomes in craniomaxillofacial surgery.

Additional Embodiments

Osseointegrated Dental Implants

Patients with poor or missing dentitions may require dental implants to improve mastication. A popular modality with increasing indications includes "osseointegrated dental implants". Osseointegrated dental implants can include, and may consist of, a two-piece permanent implant device, which is placed into either the maxilla or mandible skeleton with a power drill for placement and stability. A second piece, in the shape of a tooth is screwed onto the secure base. An embodiment of the CAPE system described above can be used to provide the dentist or surgeon real-time cephalometric feedback in an effort to restore ideal occlusion and predict optimized mastication with biomechanical predictions—as similar to maxillofacial transplantation. As such, the dentist or surgeon placing these items needs to know the bone stock quality of the jaw(s) and angle to place the framework.

Osseointegrated Craniofacial Implants and Prosthetics

Patients with severe cranial or facial disfigurement may benefit from custom implant reconstruction or be poor surgical candidates due to overwhelming co-morbidities and/or because of an accompanying poor prognosis. Therefore, to help return these patients into society, some use craniofacial implants or prosthetics as a way to restore "normalcy". Application of these three-dimensional implants and prosthetics replacing absent craniofacial features (i.e., skeletal, nose, eye, etc) may either be hand-molded/painted by an anaplastologist or printed with 3D technology by a craniofacial technician. Either way, in an embodiment, the CAPE system described above can provide a one-stop solution for patients requiring alloplastic and/or bioengineered prosthetic reconstruction for large craniomaxillofacial deformities. The craniofacial implants can be tracked as similar to a donor face-jaw-teeth segment described above. For example, pre-placement images of the implant or prosthetic onlay may be fabricated, and surgical plans may be optimized since these appliances are placed with osseointegrated devices as similar to dental implants described above—with rigid plates and screws. As such, the surgeon placing them needs to know the exact location, underlying bone stock quality, and angle to place the framework, and desires unprecedented visual feedback as to the ideal position in three-dimensional space.

Craniomaxillofacial Trauma Reconstruction

Patients suffering from acute or chronic facial disfigurement are often seen by a craniomaxillofacial surgeon. Both penetrating and/or blunt trauma may cause significant damage to the underlying facial skeleton. As such, in an embodiment, the CAPE system technology described herein allows the surgeon to assess and optimize bone fragment reduction and reconstruction with real-time feedback. In addition, fractures affecting the jaws can be aided by real-time cephalometrics in hopes to restore the patient back to their pre-trauma angle/measurements (as a way to assure proper occlusion). Navigation, as described above in an embodiment of the CAPE system, can be exceptionally helpful for orbit fractures around the eye or cranial fractures around the brain, since the nerve anatomy is delicate and consistent—which makes it applicable to the CAPE system. In summary, a surgeon (including the likes of a Plastic surgeon, ENT surgeon, oral/OMFS surgeon, oculoplastic surgeon, neurosurgeon) reducing craniofacial fractures needs to know the bone stock quality remaining, where plates/screws are best placed, and the optimal plan prior to entering the operating room.

Neurosurgical Procedures

Neurosurgeons frequently perform delicate craniotomies for access for brain surgery. Currently, there are several navigational systems available. However, none of the conventional systems include features described in the embodiments of the CAPE platform as described above. That is, the conventional systems lack the ability to assist both pre-operatively with planning AND with intra-operative navigation for execution assistance. In addition, the current neurosurgery systems require the head to be placed in antiquated "bilateral skull clamp pins" during the entire surgery. This means that before each neurosurgery procedure starts, a big 3-piece clamp is crunched onto the skull of the patient to make sure the head does not move during surgery, particularly to allow for use of the conventional navigation systems. However, embodiments of the CAPE system, such as those described above, use a small, modified rigid cranial reference mount which removes the need for using a big, bulky clamp from the field and allows the surgeon to rotate the patient's head if and when needed. To a craniofacial plastic surgeon, who often is consulted to assist with simultaneous scalp reconstruction, elimination/removal of such pins from the surgical field is a huge advantage. For example, elimination of the pins makes scalp reconstruction in the setting of neurosurgery much safer since the pins aren't present to hold back mobilization and dissection of the nearby scalp, which is needed often for complex closure. It also, reduces the risk of surgical contamination since the current setup with pins is bulky and makes surgical draping and sterility much more difficult and awkward. A small cranial mount as part of the CAPE system is a huge advancement for the field.

Congenital Deformity Correction

Unfortunately, newborns are commonly born with craniofacial deformities to either maternal exposure or genetic abnormalities. As such, they may have major development problems with their skeleton and the overlying structures (eyes, ears, nose) may therefore appear abnormal. In addition, newborns may suffer from craniosynostosis (premature fusing of their cranial sutures) which causes major shifts in the shape of their head at birth. In an embodiment, the CAPE system described above, can be utilized to address such congenital deformities, irrespective of etiology. For example, if a 16 year old needs to have major Le Fort surgery to move the central facial skeleton into better position forward to improve breathing, mastication, and appearance, use of the CAPE system technology for both pre- and intra-operatively provides a huge advancement for the field.

Head/Neck and Facial Reconstruction (ENT Surgery)

Head and neck surgeons in the specialty of Otolarygology (ENT) are frequently reconstructing facial skeletons. Reasons include post-tumor resection, facial trauma, aesthetic improvement, congenital causes and/or functional improvement (nose, mouth, eyes, etc). Therefore, this specialty would greatly benefit from use of the CAPE system technology described herein. For example, in an embodiment, use of the CAPE system can be used in a wide range of surgeries including such instances as post-trauma fracture reduction/fixation, free tissue transfer planning and execution (i.e., free flap reconstruction with microsurgical fibula flaps for large bone defects where the leg bone receives dental implants for jaw reconstruction), smaller jaw reconstruction cases with implant materials, and/or anterior skull base reconstructions with neurosurgery following tumor resection. This specialty is very diverse, and therefore the CAPE system's easy adaptability can help make it greatly valuable to this group of surgeons.

Orthognathic Surgery

Orthognathic surgery describes any of surgical procedure type moving the jaw and/or jaw-teeth segments. This is most commonly performed by either oral surgeons, oral-maxillofacial surgeons (OMFS), or plastic surgeons. It is done currently both in the hospital as an insurance case or in the outpatient setting for a fee-for-service. It may be indicated for enhanced mastication, improved aesthetics, and/or both reasons. Having the ability to plan and predict jaw movements based on biomechanical muscle (i.e., external) forces will be immensely valuable to this field. In an embodiment, surgeons can utilize the CAPE system described above to predict functional jaw movements both at time of surgery and after surgery (1, 5, 10, 20 years post-op). In addition, in an embodiment, a surgeon can utilize the CAPE system to provide real-time cephalometric feedback, which provides an advancement not seen in the conventional systems. In comparison, for the last several centuries, oral surgeons have used splints fabricated in the dental lab pre-operatively for assistance in the operating room to help confirm dental alignment as planned. This takes time (e.g., 4-6 hours to make by hand), effort, and money. In contrast to the conventional systems, surgeons utilizing the CAPE system can go to the operating room with pre-fabricated cutting guides and tracking instruments, cut the jaws where planned, and then match the teeth on the table based on real-time cephalometric feedback and biomechanical jaw simulation to predict post-operative mastication—unlike ever before. For example, use of the CAPE system will allow surgeons to know instantaneously if the aesthetic and functional angles/measurements are ideal and where they should be. In addition, the CAPE system is able to supply palatal cutting guides and pre-bent metal fixation plates (as opposed to the conventional methods that require hand bending each plate for proper shape). In summary, the CAPE system will be a "game-changer" for orthognathic surgery.

"Computer-Assisted Cranioplasty"

At least some embodiments described herein can be used for the immediate surgical repair of large cranial defects (e.g., >5 cm$^2$). For example, embodiments described herein may be used for designing, forming and implanting customized craniofacial implants following benign/malignant skull neoplasm (tumor) resection (i.e., referred to as "single-stage implant cranioplasty"). Currently, it is challenging to reconstruct such patients with pre-fabricated implants using conventional methods since the actual size/shape of the defect site is unknown until the tumor is removed. Accordingly, use of a computer-assisted surgical system of an embodiment may significantly reduce the intraoperative time used for reshaping/resizing the customized implant. For example, embodiments provide visualization related to the tumor, the resulting skull defect, and the reshaped implant for exact positioning. In other words, in an embodiment, a Computer-Assisted Planning and Execution (CAPE) system that can be utilized for Le Fort-based, Face-Jaw-Teeth transplantation may also be used for improving both the pre-operative planning and intra-operative execution of single-stage implant cranioplasties. Cranioplasties may be performed to reconstruct large defects following stroke, trauma, aneurysmal bleeding, bone flap removal for infection, and oncological ablation. However, oncological defects are commonly reconstructed with "off-the-shelf" materials, as opposed to using a pre-fabricated customized implant—simply because the exact defect size/shape is unknown. With this in mind, embodiments described herein include a computer-assisted algorithm that may allow surgeons to reconstruct tumor defects with pre-customized cranial implants (CCIs) for an ideal result.

Nearly 250,000 primary brain tumors/skull-based neoplasms are diagnosed each year resulting in a range of 4500-5000 second-stage implant cranioplasties/year. Unfortunately, the common tumor defect cranioplasty is reconstructed with on-table manipulation of titanium mesh, liquid polymethylmethacrylate (PMMA), liquid hydroxyapatite/bone cement (HA) or autologous split-thickness calvarial bone grafts (ref), which forces the surgeon to shape/mold these materials to an approximate size/shape. Expectingly, this results in some form of craniofacial asymmetry and a post-operative appearance which is suboptimal. Furthermore, the difficult shaping process may take several hours—which in turn increases anesthesia, total blood loss, risk for infection, morbidity, and all costs associated with longer operative times. Therefore, there is significant opportunity to extend this CAPE to thousands of patients.

In the year 2002, the advent of computer-aided design and manufacturing (CAD/CAM) was used for the first time to pre-emptively match the contralateral, non-operated skull for ideal contour and appearance, which provided for the use of CCIs. However, cranioplasties with such CCIs can only be performed as "second stage" operations during which a clinician, such as a surgeon, ensures that the CCI fits perfectly into the skull defect. Recent developments have demonstrated the feasibility of CCIs for "single-stage cranioplasty", but this involves using a handheld bur to shave down the pre-fabricated implant artistically. However, challenges in both assessing and predicting each tumor-resection deformity pre-surgery still limits the applicability of CCIs in this patient population. For example, challenges such as 1) unknown exact tumor size, 2) unknown growth from time of pre-op CT scan-to-actual day of surgery, and 3) the unknown resection margins needed to minimize local recurrence. For these cases, the CCI would need to be reshaped/resized intraoperatively from a size slightly larger than expected—which is a process that may take several (2-4) hours. However, there are no established planning and execution systems available to assist these single-stage reconstructions. Accordingly, embodiments described herein may be used by surgeons in performing single-stage cranioplasty following oncological resection. In other words, embodiments include algorithms for real-time updates related to single-stage customized implant cranioplasty. For example, in an embodiment, there is a Computer-Assisted Planning and Execution (CAPE) system, which is a SINGLE, seamless platform capable of being used for both planning (pre-op use) and navigation (intra-op use) which overcomes the limitations of conventional systems that do either one or the other. In addition, embodiments include novel hardware such as trackable cutting guides and rigid cranial reference mount.

Computer-Assisted Transplantation System

In an embodiment, there is a computer-assisted transplantation system 1500 such as the system 2000 depicted in FIGS. 15A-15G and described above. It is noted that components of system 2000 may be combined with or interchanged with components of system 200 illustrated in FIGS. 2A-2G. The system can include a donor sub-system 2000-D and a recipient sub-system 2000-R. The donor sub-system may include a first reference unit 2005-D having a first trackable element 2001-D which may be integrated with, attached to, or detachably connected to a mount, such as a cranial reference mount 2003-D. The first reference unit 2005-D may be attached at a predetermined location on a donor being 2006 anatomy, such as a predetermined skeletal feature 2009-D, for example, a location of the donor's skull. The donor sub-system 2000-D may also include a fragment reference unit having a second trackable element 2001-D'. The fragment reference unit may be attached on a predetermined location on the donor being 2006 anatomy, such as at a predetermined location on a portion 2011-D of the donor being's anatomy that is to be fragmented from the donor being and transplanted onto a recipient being. The donor sub-system 2000-D may also include a first detector 2013-D that may be configured to provide at least one of a first signal 2091 as shown in FIG. 15H corresponding to a detected location of one or more of the first trackable element 2001-D and the second trackable element 2001-D'.

The recipient sub-system 2000-R may include a second reference unit 2005-R having a third trackable element 2001-R. The second reference unit 2005-R may be attached at a predetermined location on a recipient being 2008 anatomy, such as at a predetermined skeletal feature 2009-R, for example, a location 2010 of the recipient's skull via a mount such as a cranial reference mount 2003-R. The recipient sub-system 2000-R may also include a second detector 2013-R configured to provide at least one of a second signal 2093, as shown in FIG. 15H, corresponding to a detected location of at least the third trackable element 2001-R.

The donor sub-system 2000-D may further include a cutting guide 2007-D having a fourth trackable element 2017-D. The cutting guides described herein may be a surgical guide assembly having an attachment device configured to be coupled to a bone. A cut location indicator is coupled to the attachment device. The cut location indicator identifies a location where the bone is to be cut. An arm is coupled to the attachment device, the cut location indicator, or both. A support structure is coupled to the arm. The support structure is configured to have a tracking element coupled thereto.

The donor sub-system may further include a first computer 2015-D that receives the at least one first signal 2091. The recipient sub-system 2000-R may further include a second computer 2015-R that receives the at least one second signal 2093. The at least one first signal 2091 and the at least one second signal 2093 may be communicated between the detectors and computers via a communications link, as indicated by the dashed double-headed arrow in FIG. 15F, which may include data transmission wires and/or wireless transmissions either of which may be communicated through a network, such as a LAN or WAN network, including communication over an intranet or over the internet, including TCP/IP data transfer. In an example, a communications link allows the first computer 2015-D and the second computer 2015-R to communicate with one another.

Figure 15A:
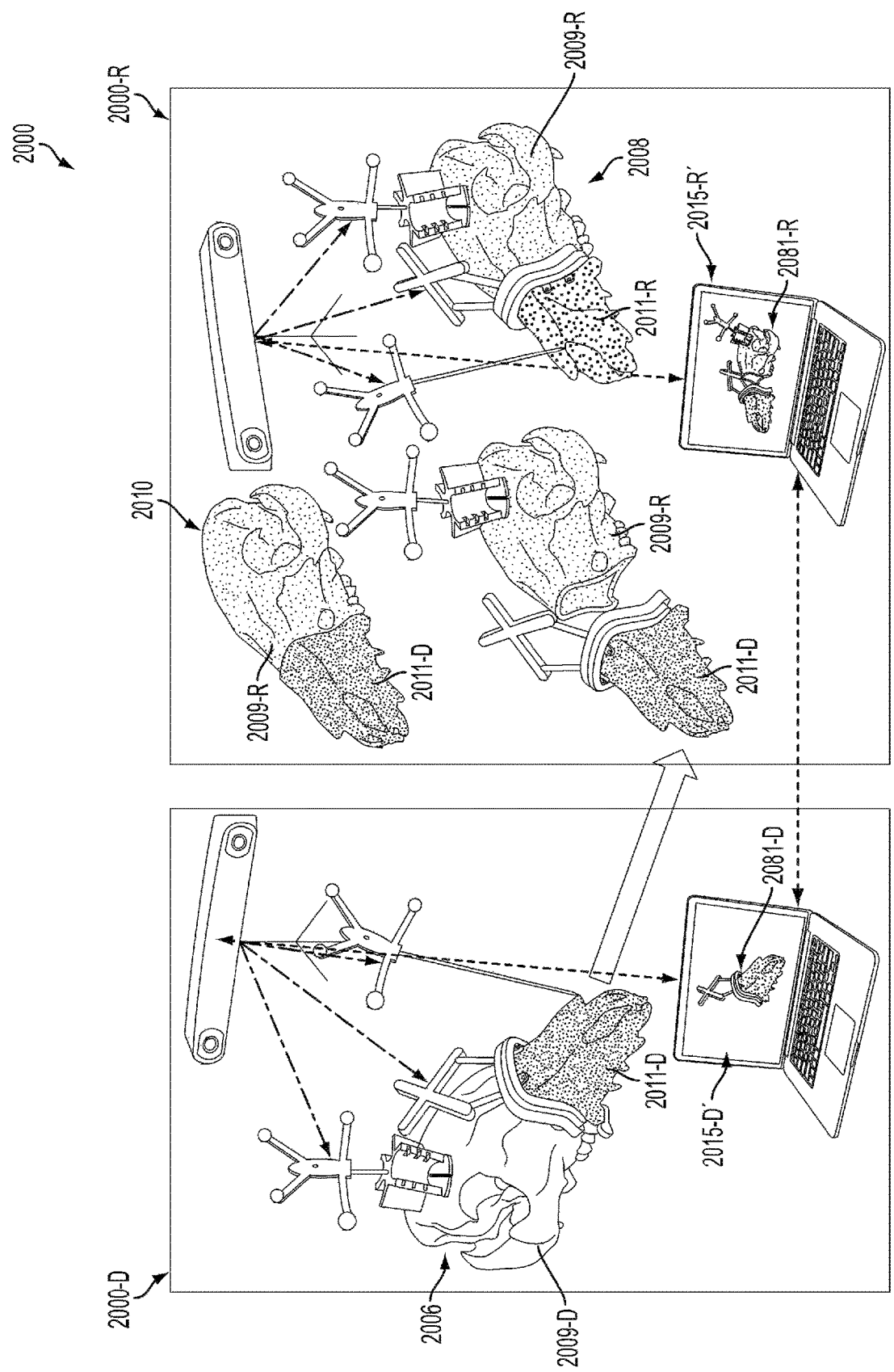
FIGS. 15A-15C provide a schematic overview of a surgical system similar to that of FIGS. 2A-2C.
Figure 15B:
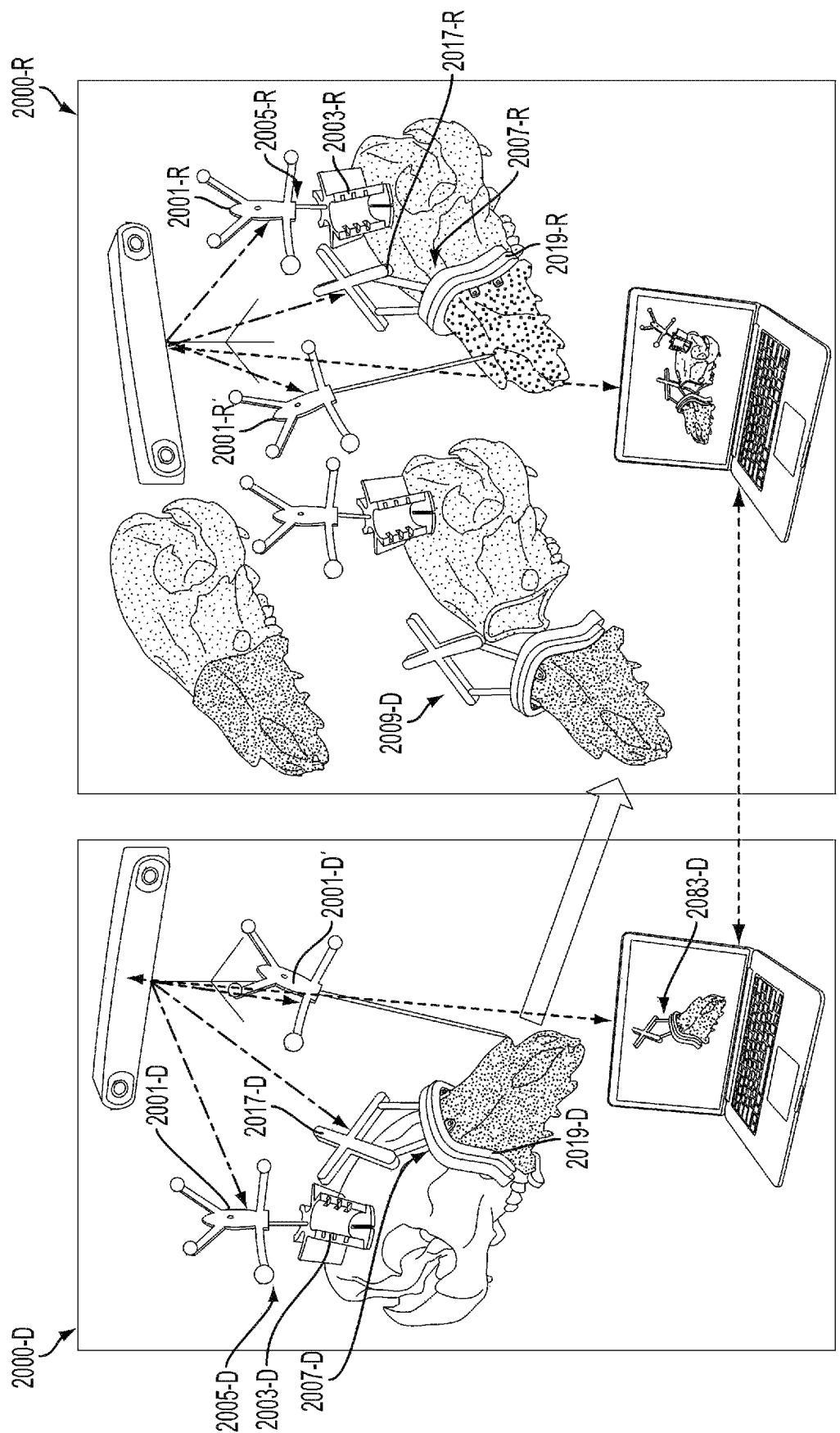
Figures 15C, 15D, 15E, 15F, 15G, 15H:
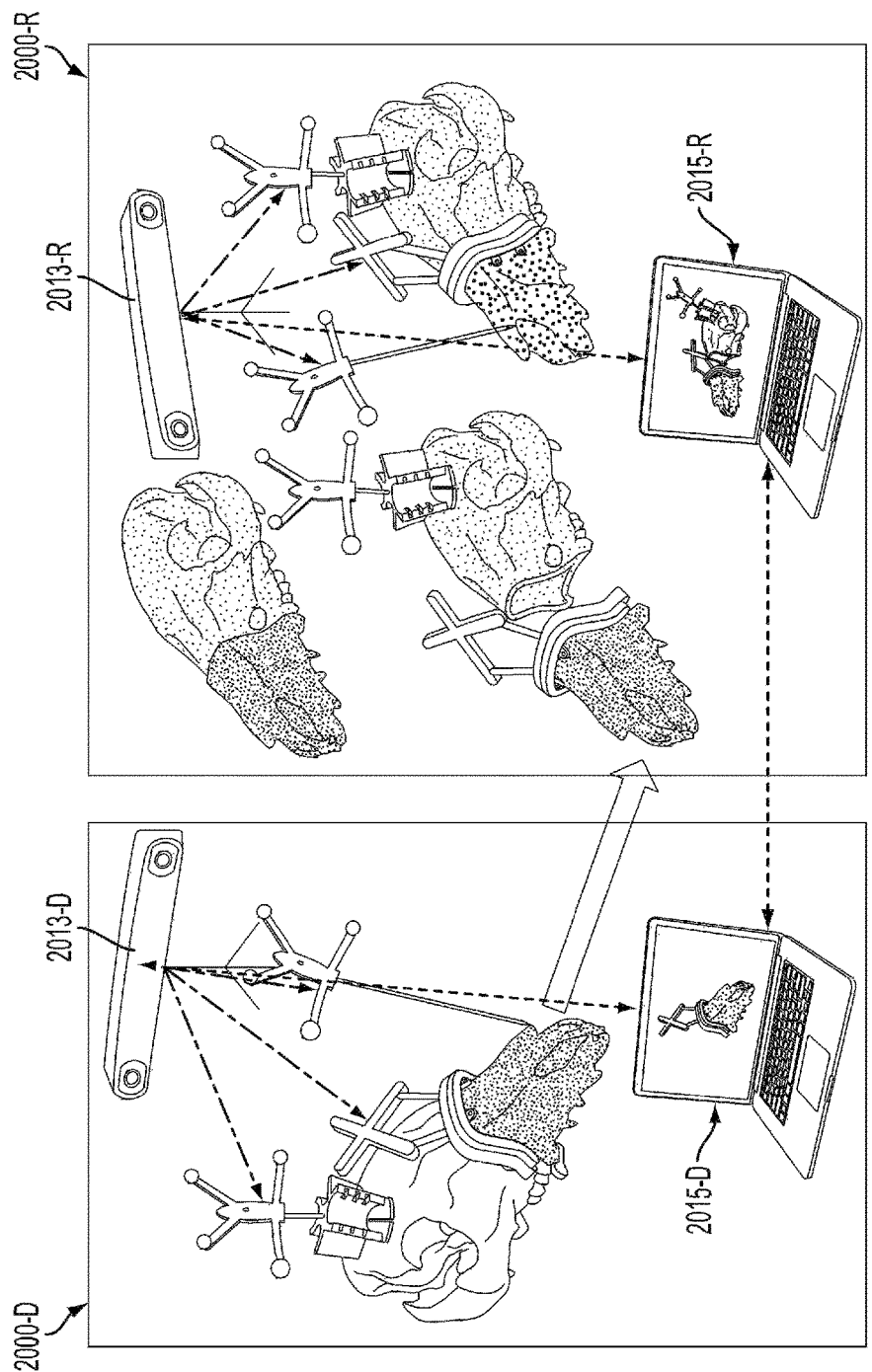
FIGS. 15D-15H are graphical representations of some components and/or features of the surgical system of FIGS. 15A-15C.

The first detector 2013-D, the second detector 2013-R, or both may be an optical tracker, a magnetic tracker or both an optical tracker and a magnetic tracker as generally shown in FIG. 15G as 2013, and may be utilized in the system to perform a detecting function, as indicated by the double-headed arrow in FIG. 15, for detecting locations of items. Optical trackers typically emit and capture light in the invisible (infrared) electromagnetic spectrum. Trackable fiducials used with these systems can include passive (i.e., reflective) or active (i.e., those that actively emit infrared light) markers. Using specific geometries known to the camera, the pose of a reference can be tracked through the field of view. An example system is the NDI Polaris available from Northern Digital, Inc. (Ontario, Canada). Magnetic trackers rely on a magnetic field generator and (typically) a passive coil architecture. The field generator creates a time-varying field, which induces a current in the passive sensor. This current is measured and, through a calibration procedure, used to identify up to a 6-dof pose of the sensor. An example system is the NDI Aurora available from Northern Digital, Inc. (Ontario, Canada).

One or more of the first trackable element 2001-D, the second trackable element 2001-D', the third trackable element 2001-R, and the fourth trackable element 2017-D may be an IR reflector or an IR emitter, as generally shown as 2001 in FIG. 15D, each of which may be detachably connected to an attachment surface such as a mount, including a cranial reference mount 2003, which may form part of a reference unit 20005 as generally shown in FIG. 15E. As an example, an IR reflector may be a detachably connected surface, such as a sphere. As an example, an IR emitter may be a light emitting diode configured to emit infrared light.

The first and second computers may be selected from a desktop computer, a network computer, a mainframe, a server, or a laptop. The first and second computers may be configured to access at least one computer readable reconstruction of at least one object, such as a being's anatomy, or at least portions of the being's anatomy, for example, a first computer readable reconstruction 2081-D and a second computer readable reconstruction 2801-R. The computer readable reconstruction may include three-dimensional (3D) views, such as those created by scanning a patient via, for example, CT scan. At least one display, such as a first display 2015-D' may be connected to the first computer 2015-D. The display may be configured to represent the computer readable reconstruction. The first computer may include at least one memory to store data and instructions, and at least one processor configured to access the at least one memory and to execute first instructions 1600.

Figure 16:
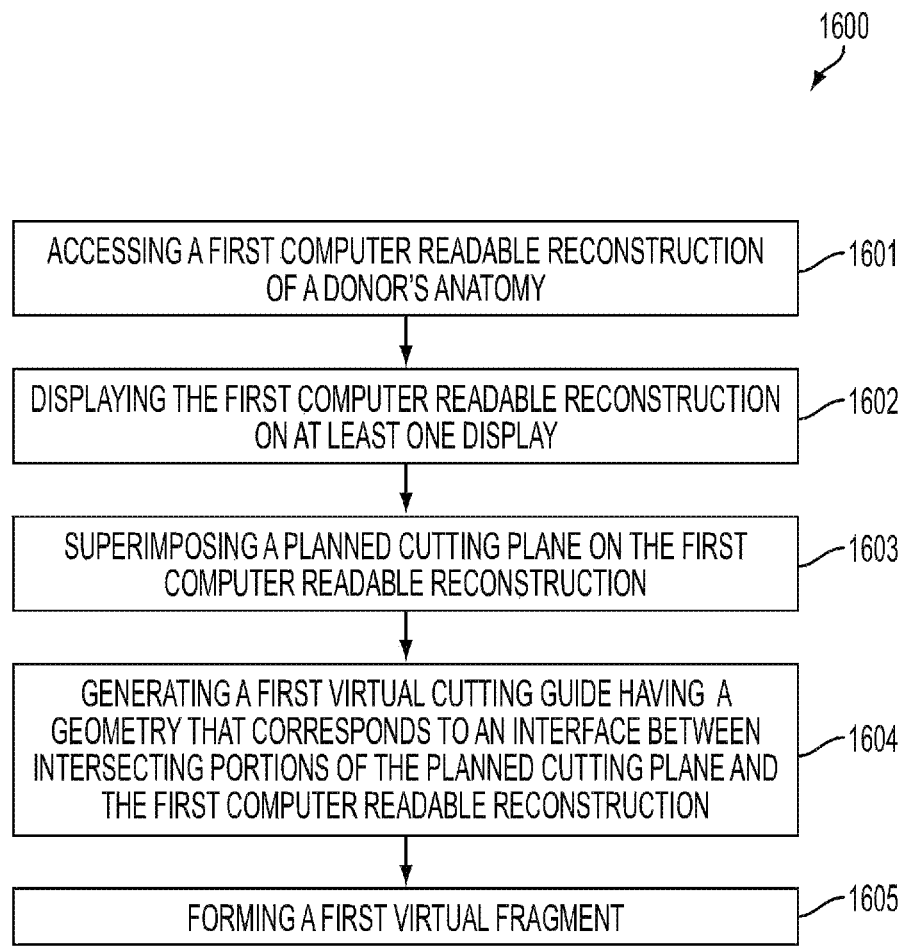
FIG. 16 is a flow chart depicting instructions that may be executed by a processor.

First instructions 1600 may include one or more of the steps included in the flowchart on FIG. 16. For purposes of providing examples, some of the steps are described below with reference to components of system 2000 from FIGS. 15A-15G. In an embodiment, first instructions 1600 include accessing a first computer readable reconstruction of a donor anatomy at 1601, and displaying the first computer readable reconstruction on at least one display at 1602, such as the first display 2015-D'. The first computer readable reconstruction may include a first orientation that is updated based on a physical location of at least one of the first trackable element 2001-D and the second trackable element 2001-D' as detected by the first detector 2013-D. The first instructions 1600 may further include superimposing a planned cutting plane (such as cutting plane 403 of FIG. 4A) on the first computer readable reconstruction at 1603. The first instructions 1600 may further include generating a first virtual cutting guide 2083-D having a geometry that corresponds to an interface between intersecting portions of the planned cutting plane and the first computer readable reconstruction at 1604.

The first instructions 1600 may further include controlling at least one device for manufacturing a cutting guide, such as cutting guide 207-D, according to the geometry of the first virtual cutting guide 2083-D at 1604. The device may be any manufacturing device that fabricates an object based on instructions, such as computer readable instructions, for example, instructions provided in digital data, including any device that utilizes additive or subtractive manufacturing technologies, such as those that fabricate an object from appropriately approved materials for medical use. Accordingly, the at least one device may be an additive manufacturing device, such as a 3D printer, or another kind of manufacturing device, including subtractive manufacturing device, such as a CNC machine. Examples of additive manufacturing technologies may include vat polymerization (e.g., PROJET® 6000, 7000, 8000 available from 3D Systems Corp., Rock Hill, S.C.), materials jetting (e.g., Objet 500 or Eden 250, each available from Stratasys, Ltd., Eden Prairie, Minn.), powder binding (e.g., PROJET® 460, 650 available from 3D Systems Corp., Rock Hill, S.C.), powder fusion (e.g., EBM® available from Arcam AB, Sweden), material extrusion (Fortus 250, 400, available from Stratasys, Ltd., Eden Prairie, Minn.), or any one denoted by the ASTM F42 committee on additive manufacturing. Accordingly, system 2000 may include a device (not shown) for manufacturing components, such as cutting guides, reference units and/or the trackable elements, and the device may be connected to at least one of the first computer and the second computer via the communications link described above. The first instructions may also include generating a computer readable file that contains instructions for manufacturing the cutting guide, and/or contains dimensions of a cutting guide based on the geometry of the first virtual cutting guide.

The first instruction 1600 may also include forming a first virtual fragment 2011-D by, for example, segmenting the computer readable reconstruction of the donor anatomy along portions of the computer readable reconstruction that intersect with the planned cutting plane, at 1605. In an embodiment, the first virtual fragment 2011-D may include a third orientation that is updated based on a physical location of at least one of the first trackable element 2001-D and the second trackable element 2001-D' as detected by the first detector 2013-D.

In an embodiment, at least one display, such as a second display 2015-R' is connected to a second computer, such as second computer 2015-R. The second computer may include at least one memory to store data and instructions, and at least one processor configured to access the at least one memory and to execute second instructions 1700.

Figure 17:
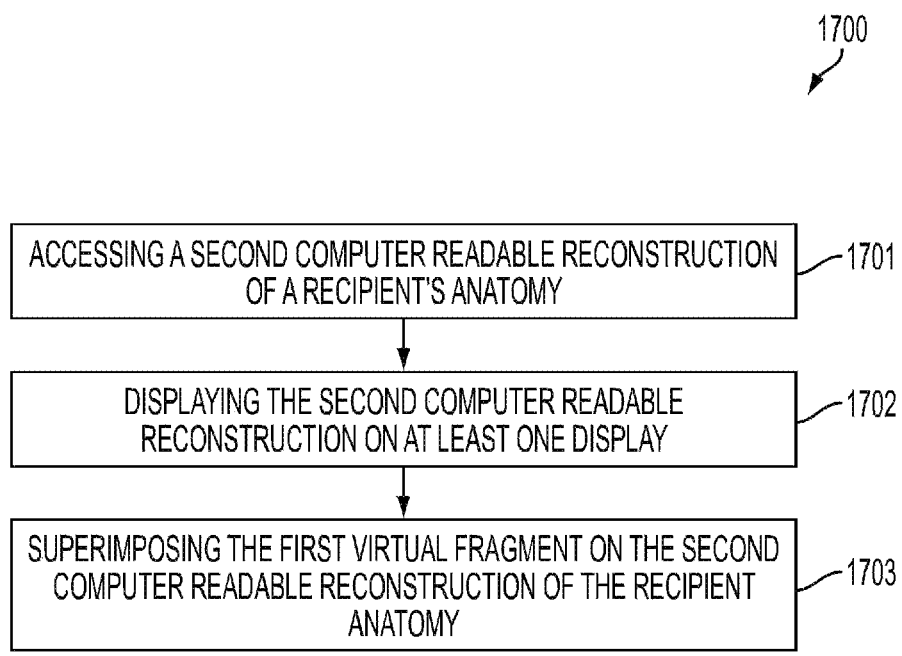
FIG. 17 is a flow chart depicting instructions that may be executed by a process.

Second instructions 1700 may include one or more of the steps included in the flowchart on FIG. 17. For purposes of providing examples, some of the steps of instructions 1700 are described with reference to components of system 2000 from FIGS. 15A-15H. The second instructions 1700 may include accessing a second computer readable reconstruction of a recipient anatomy, such as second computer readable reconstruction 2081-R at 1701. Second instructions 1700 may further include displaying the second computer readable reconstruction on the at least one display, such as the second display 2015-R at 1702. The second computer readable reconstruction may include a second orientation that is updated based on a physical location of the third trackable element 2001-R as detected by the second detector 2013-R.

During a surgical procedure, such as a transplantation of a anatomical feature from a donor being onto the anatomy of a recipient being, it is useful to track the location of the fragment relative to the anatomy of the recipient being before, during and/or after the transplantation. Accordingly, in the system 2000, the second signal 2093 may further correspond to a location of the second trackable element 2001-D as detected by the second detector 2013-R. Thus, the second instructions 1700 may also include superimposing the first virtual fragment 2011-D on the second computer readable reconstruction 2008 of the recipient anatomy at 1703, for example, with an orientation that is updated based on a physical location of the second trackable element 2001-D' and the third trackable element 2001-R as sensed by the second detector 2013-R.

Figure 18:
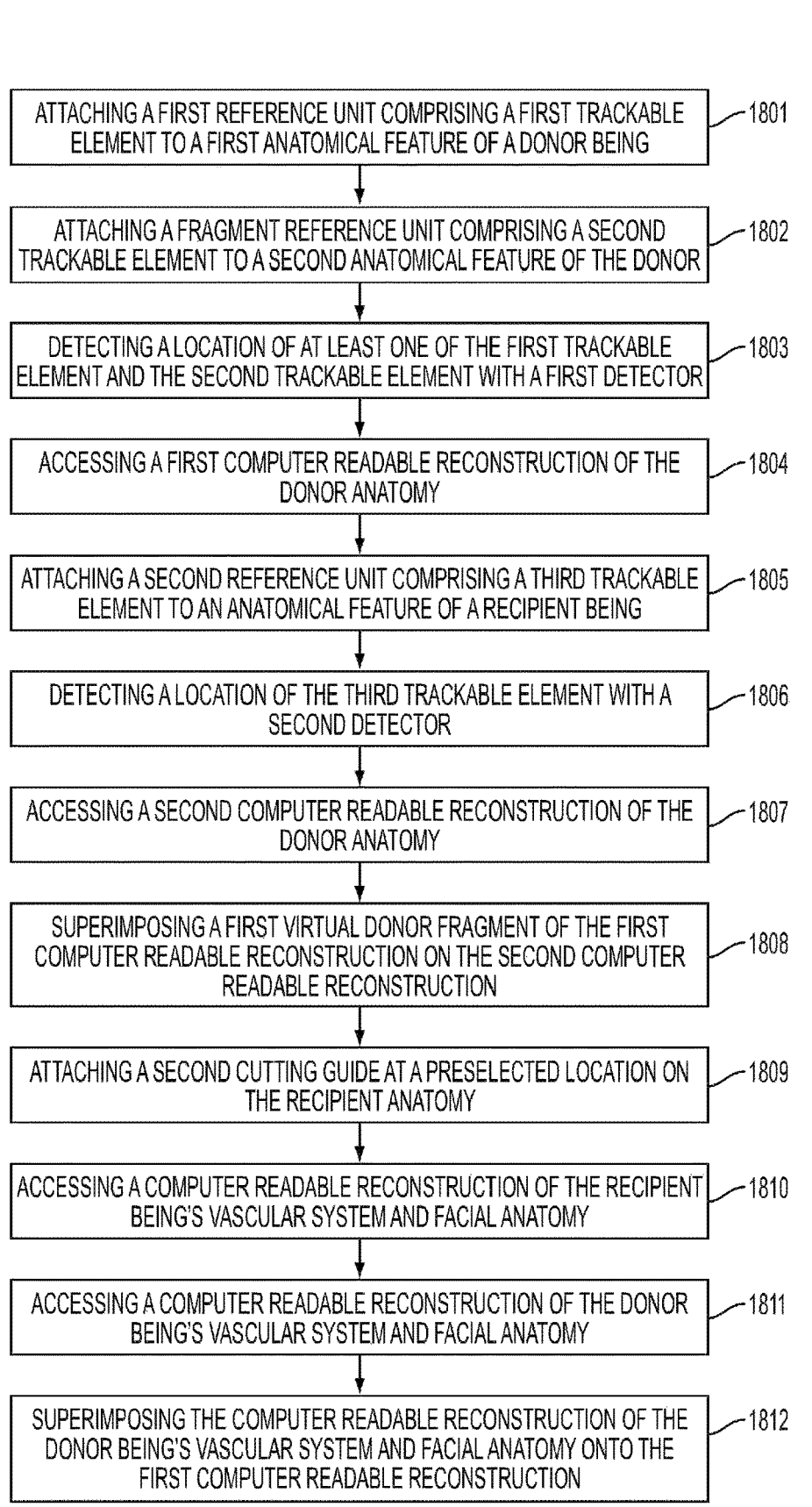
FIG. 18 is a flow chart depicting a surgical method.

FIG. 18 is a flow chart depicting a computer-assisted transplantation method 1800. The method 1800 may include steps for interacting with, for example, using the system 2000. In an example, the method can include attaching a first reference unit comprising a first trackable element to a first anatomical feature of a donor being at 1801. The method 1800 includes attaching a fragment reference unit comprising a second trackable element to a second anatomical feature of the donor at 1802. The method 1800 includes detecting a location of at least one of the first trackable element and the second trackable element with a first detector at 1803. As described above, the first detector may be configured to provide at least one of a first signal corresponding to the detected location of at least one of the first trackable element and the second trackable element. The method 1800 may include accessing a first computer readable reconstruction of the donor anatomy at 1804. As described above, the first computer readable reconstruction may include a first orientation that is updated based on a physical location of at least one of the first trackable element and the second trackable element as detected by the first detector. The method 1800 may include attaching a second reference unit comprising a third trackable element to an anatomical feature of a recipient being at 1805. The method 1800 may include detecting a location of the third trackable element with a second detector at 1806. As described above, the second detector may be configured to provide at least one of a second signal corresponding to a detected location of at least the third trackable element. The method 1800 may also include accessing a second computer readable reconstruction of the recipient anatomy at 1807. As described above, the second computer readable reconstruction may include a second orientation that is updated based on a physical location of the third trackable element detected by the second detector. The method 1800 may include superimposing a first virtual donor fragment of the first computer readable reconstruction on the second computer readable reconstruction at 1808. The method 1800 may also include attaching a second cutting guide at a preselected location on the recipient anatomy at 1809. The second cutting guide may be formed according the methods described above, except may be based on a geometry of an intersection of a planned cutting plane that is superimposed on the second computer readable reconstruction of the recipient's anatomy. In other words, the second cutting guide may be custom designed for attaching on the recipients anatomy. Accordingly, the second cutting guide may include an attachment surface configured for attaching to an anatomical feature and a fifth trackable element. Accordingly, the second signal may further correspond to a detected location of the fifth trackable element.

The method 1800 may also include accessing a computer readable reconstruction of the recipient being's vascular system and facial anatomy at 1810, accessing a computer readable reconstruction of the donor being's vascular system and facial anatomy at 1811, and superimposing the computer readable reconstruction of the donor being's vascular system and facial anatomy onto the first computer readable reconstruction at 1812.

The described method may be utilized during a surgical procedure, such as a surgical transplantation procedure or an implant-based cranioplasty. Accordingly, there is a donor being (or a custom, 3D craniofacial implant made of either alloplastic materials or biologic tissue engineered cells—which is analogous to the donor's face-jaw-teeth segment in this case) and a recipient being on whom the surgical procedure is performed. In an example, the donor provides an anatomical feature and the recipient receives the anatomical feature. In an example, the donor being is a male being and the recipient is a female being. In an example, the donor being is a female being and the recipient is a male being. In an example, the donor and the recipient are the same sex. Although in some transplantations, the donor being and recipient being are two separate beings, the invention is not so limited. Accordingly, in an example the donor being and the recipient being may be i) the same being, or ii) different beings.

Figure 19:
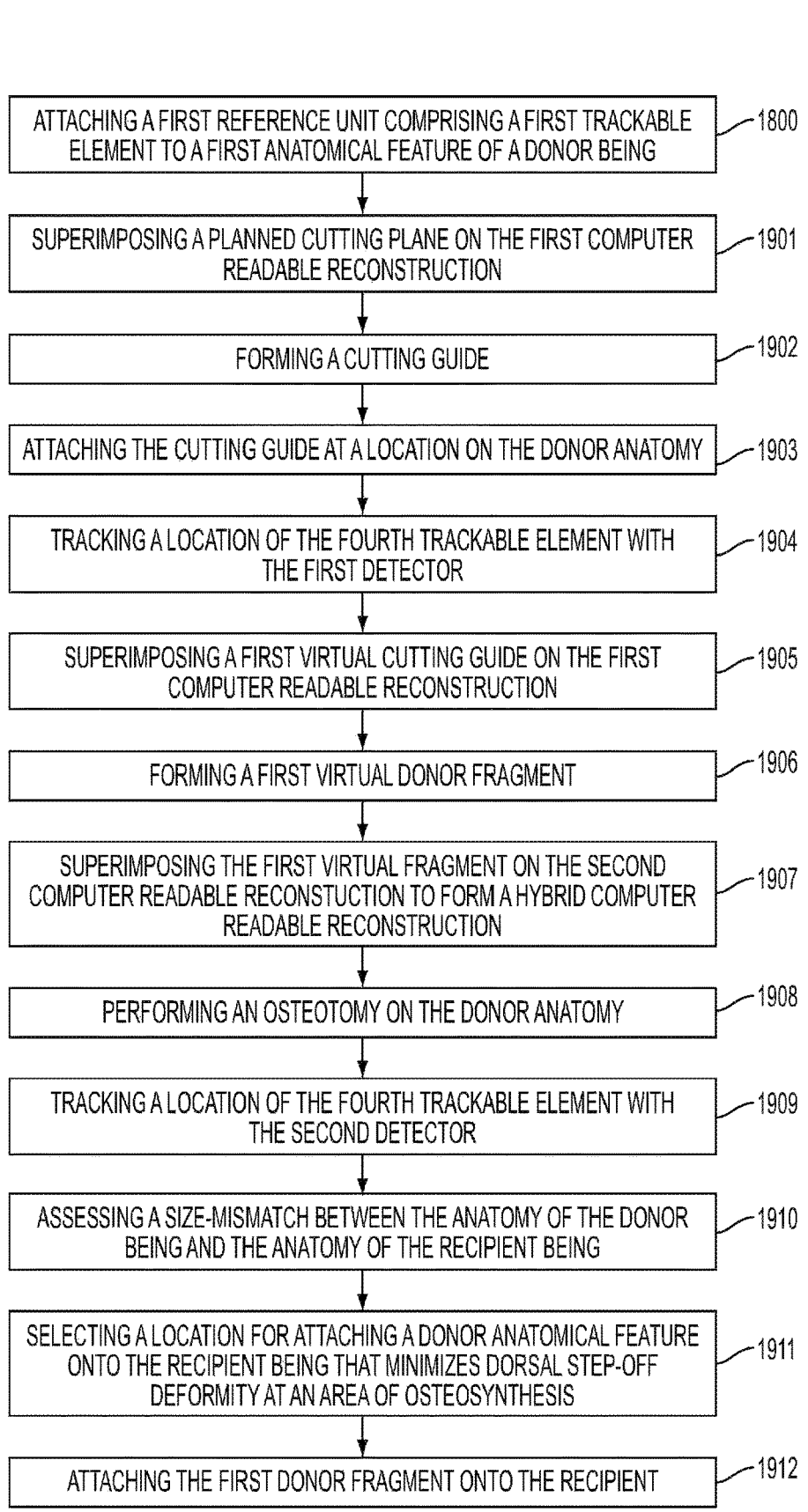
FIG. 19 is a flow chart depicting a surgical method.

FIG. 19 is a flow chart depicting a computer-assisted transplantation method 1900 which may include all the steps of method 1800, for example, including step 1801. The method 1900 may also include superimposing a planned cutting plane on the first computer readable reconstruction at 1901, and forming a cutting guide at 1902. As described above for system 2000, the cutting guide may include at least one attachment configured in a geometry defined by intersecting portions of the planned cutting plane and the first computer readable reconstruction. Additionally, the cutting guide may further include a fourth trackable element. As described above, the second signal may further correspond to a detected location of the fourth trackable element. The method 1900 may also include attaching the cutting guide at a location on the donor anatomy at 1903, tracking a location of the fourth trackable element with the first detector at 1904, and superimposing a first virtual cutting guide on the first computer readable reconstruction at 1905. As described above for system 2000, the first computer readable reconstruction may have an orientation that is updated based on at least one of the first trackable element, the second trackable element and the fourth trackable element. The method 1900 may also include forming a first virtual donor fragment at 1906, for example, by segmenting the first computer readable reconstruction at an interface of the planned cutting plane and the first computer readable reconstruction. The method 1900 may also include superimposing the first virtual fragment on the second computer readable reconstruction to form a hybrid computer readable reconstruction at 1907.

The method 1900 may further include performing an osteotomy on the donor anatomy at 1908. The osteotomy may include, among other steps, cutting the donor anatomy along a cutting path defined by the first cutting guide and removing a first donor fragment from the donor anatomy. The first donor fragment may be separated from the donor anatomy along the cutting path and comprising the second anatomical feature. The method 1900 may further include tracking a location of the fourth trackable element with the second detector at 1909.

The method 1900 may also include assessing a size-mismatch by measuring inconsistent skeletal interfaces between the anatomy of the donor being, for example, by measuring a dorsal maxillary interface, between the anatomy of the donor being and the anatomy of the recipient being at 1910, and selecting a location for attaching a donor anatomical feature onto the recipient being that minimizes the size mismatch, such as, step-off deformity, for example, that minimizing the dorsal step-off deformity, at an area of osteosynthesis at 1911. The method 1900 may also include attaching the first donor fragment onto the recipient at 1912, for example, to form recipient fragment 2011-R. In an example, superimposing the first virtual fragment on the second computer readable reconstruction of the recipient anatomy may include performing an automated cephalometric computation for the hybrid reconstruction.

The terms "couple," "coupled," "connect," "connection," "connected," "in connection with," and "connecting" refer to "in direct connection with" or "in connection with via one or more intermediate elements or members." Furthermore, to the extent that the terms "including", "includes", "having", "has", "with", or variants thereof are used in either the detailed description and the claims, such terms are intended to be inclusive in a manner similar to the term "comprising." As used herein, the phrase "at least one of" or "one or more of", for example, A, B, and C means any of the following: either A, B, or C alone; or combinations of two, such as A and B, B and C, and A and C; or combinations of three A, B and C.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-assisted surgical system for performing craniomaxillofacial surgery, comprising:
    an implant sub-system comprising:
        a first reference unit composed of a trackable element, and
        a first detector configured to provide a first signal corresponding to a detected location of the first reference unit;
    a recipient sub-system comprising:
        a second reference unit composed of a trackable element, and
        a second detector configured to provide a second signal corresponding to a detected location the second reference unit; and
    a first computer and at least one display connected to the first computer, wherein the first computer comprises:
        at least one memory to store data and instructions, and
        at least one processor configured to access the at least one memory and to execute first instructions, the first instructions comprising:
            accessing a first computer readable reconstruction of an implant, and
            displaying the first computer readable reconstruction on the at least one display, wherein the first computer readable reconstruction comprises a first orientation that is updated based on a physical location of the first reference unit as detected by the first detector.

2. The system of claim 1, wherein the implant sub-system comprises the first computer that receives the at least one first signal, and wherein the recipient sub-system further comprises a second computer that receives the at least one second signal.

3. The system of claim 2, further comprising a communications link that allows the first computer and the second computer to communicate with one another.

4. The system of claim 1, wherein the first detector, the second detector, or both the first and second detectors comprise an optical tracker, a magnetic tracker or both an optical tracker and a magnetic tracker.

5. The system of claim 1, wherein one or more of the first trackable element, the second trackable element, and the third trackable element comprise an IR reflector or an IR emitter.

6. A computer-assisted method for performing craniomaxillofacial surgery, comprising:
    attaching a first reference unit comprising a first trackable element to an implant;
    attaching a fragment reference unit comprising a second trackable element to the implant;
    detecting a location of at least one of the first trackable element and the second trackable element with a first detector, the first detector configured to provide at least one of a first signal corresponding to the detected location of at least one of the first trackable element and the second trackable element;
    accessing a first computer readable reconstruction of the implant, wherein the first computer readable reconstruction comprises a first orientation that is updated based on a physical location of at least one of the first trackable element and the second trackable element as detected by the first detector;

attaching a second reference unit comprising a third trackable element to an anatomical feature of a recipient being;

detecting a location of the third trackable element with a second detector, the second detector configured to provide at least one of a second signal corresponding to a detected location of at least the third trackable element;

accessing a second computer readable reconstruction of the recipient anatomy, wherein the second computer readable reconstruction comprises a second orientation that is updated based on a physical location of the third trackable element detected by the second detector; and superimposing the first computer readable reconstruction on the second computer readable reconstruction.

7. The method of claim 6, further including attaching the first donor fragment onto the recipient.

8. The method of claim 7, further comprising:
assessing a size-mismatch by measuring inconsistent skeletal interfaces between the implant and the anatomy of the recipient being, and
selecting a location for attaching the implant onto the recipient being that minimizes a step-off deformity at an area of osteosynthesis.

9. The method of claim 6, further comprising performing an automated cephalometric computation, a biomechanical simulation, or both for the hybrid reconstruction.

10. The method of claim 6, further comprising attaching a second cutting guide at a preselected location on the recipient anatomy, wherein the second cutting guide comprises:
an attachment surface configured for attaching to an anatomical feature and
a fifth trackable element; and
wherein the second signal further corresponds to a detected location of the fifth trackable element.

11. The method of claim 6, further comprising accessing a computer readable reconstruction of the recipient being's vascular system and facial anatomy.

* * * * *